(12) United States Patent
Bobey et al.

(10) Patent No.: US 9,675,775 B2
(45) Date of Patent: Jun. 13, 2017

(54) FILTRATION UNIT USEABLE IN A RESPIRATORY THERAPY DEVICE

(71) Applicant: Hill-Rom Services PTE Ltd., Singapore (SG)

(72) Inventors: John Alan Bobey, Charleston, SC (US); Brian E. Byrd, Summerville, SC (US)

(73) Assignee: Hill-ROM Services PTE Limited, Singapore (SG)

( * ) Notice: Subject to any disclaimer, the term of this patent is extended or adjusted under 35 U.S.C. 154(b) by 0 days.

(21) Appl. No.: 15/002,811

(22) Filed: Jan. 21, 2016

(65) Prior Publication Data

US 2016/0136378 A1 May 19, 2016

Related U.S. Application Data

(62) Division of application No. 13/685,103, filed on Nov. 26, 2012, now Pat. No. 9,272,115.

(51) Int. Cl.
*A61M 16/14* (2006.01)
*A61M 16/10* (2006.01)
(Continued)

(52) U.S. Cl.
CPC .......... *A61M 16/105* (2013.01); *A61M 11/06* (2013.01); *A61M 16/0488* (2013.01);
(Continued)

(58) Field of Classification Search
CPC ..... A61B 5/0836; A61B 5/097; A61B 5/6819; A61M 11/00; A61M 11/06; A61M 15/08; A61M 16/00; A61M 16/0069; A61M 16/009; A61M 16/04; A61M 16/0488; A61M 16/06; A61M 16/0666; A61M 16/0672; A61M 16/0677; A61M 16/08; A61M 16/085; A61M 16/0858;
(Continued)

(56) References Cited

U.S. PATENT DOCUMENTS 3,932,153 A * 1/1976 Byrns ............... A61M 16/1055
128/205.29
5,390,668 A * 2/1995 Lehman ................. A61B 5/097
128/205.27
(Continued)

FOREIGN PATENT DOCUMENTS

EP 2316514 A1 5/2011

OTHER PUBLICATIONS

User Manual: The MetaNeb System; From Hill-Rom; Product No. PMN3; 162902 Rev May 4, 2012.
(Continued)

*Primary Examiner* — Annette Dixon
(74) *Attorney, Agent, or Firm* — Kenneth C. Baran

(57) ABSTRACT

A filtration module for comprises a filter housing defining two or more filter compartments. The housing has an input side with a gas inlet in fluid communication with each of the filter compartments and a gas outlet in fluid communication with each of the filter compartments. A filter element resides in each of the compartments intermediate the gas inlet to the compartment and the gas outlet from the compartment. One application for the filtration module is a respiratory therapy device.

14 Claims, 24 Drawing Sheets

(51) Int. Cl.
*A61M 16/04* (2006.01)
*A61M 16/08* (2006.01)
*A61M 11/06* (2006.01)
*A61M 16/12* (2006.01)
*A61M 16/00* (2006.01)

(52) U.S. Cl.
CPC .... *A61M 16/0816* (2013.01); *A61M 16/0858* (2014.02); *A61M 16/127* (2014.02); *A61M 16/14* (2013.01); *A61M 16/0057* (2013.01); *A61M 16/0875* (2013.01); *A61M 16/107* (2014.02); *A61M 2202/0208* (2013.01)

(58) Field of Classification Search
CPC ................ A61M 16/10; A61M 16/105; A61M 16/1055; A61M 16/1065; A61M 16/107; A61M 16/12; A61M 16/125; A61M 16/127; A61M 16/14; A61M 16/202; A61M 16/0057; A61M 16/0093; A61M 16/0683; A61M 16/0816; A61M 16/0875; A61M 16/1045; A61M 16/106; A61M 16/16; A61M 16/22; A61M 2016/0021; A61M 2016/0039; A61M 2016/0042; A61M 2202/0007; A61M 2202/0208; A62B 17/00; A62B 17/04; A62B 18/00; A62B 18/006; A62B 18/02; A62B 23/00; A62B 23/02; A62B 23/025; A62B 7/00; A62B 7/02; A62B 7/04; A62B 7/10; A62B 7/12; A62B 9/00; A62B 9/003; A62B 9/06

USPC ............ 128/200.24, 201.25, 201.28, 204.18, 128/204.21, 204.23, 204.26, 205.12, 128/205.24, 205.25, 205.27, 205.29, 128/206.11, 206.16, 206.17, 206.27, 128/206.29, 207.11, 207.12, 207.18; 96/108

See application file for complete search history.

(56) References Cited

U.S. PATENT DOCUMENTS

| | | | |
|---|---|---|---|
| 7,007,692 | B2 | 3/2006 | Aylsworth |
| 7,114,497 | B2 | 10/2006 | Aylsworth |
| 7,305,988 | B2 | 12/2007 | Acker |
| 7,909,033 | B2 | 3/2011 | Faram |
| 9,272,115 | B2 | 3/2016 | Bobey et al. |
| 2005/0257794 | A1* | 11/2005 | Aylsworth ........ A61M 16/0666 128/207.18 |
| 2006/0169281 | A1 | 8/2006 | Aylsworth |
| 2009/0188500 | A1 | 7/2009 | Faram |
| 2010/0269828 | A1 | 10/2010 | Orr |
| 2011/0100360 | A1 | 5/2011 | Faram |

OTHER PUBLICATIONS

User Manual the METANEB® System From Hill-Rom; Product No. PMN3; 162902 Rev. 4; May 2012; Manufactured by: Hill-Rom Services Private Limited 1 Yishun Avenue 7 Singapore 768923.

* cited by examiner

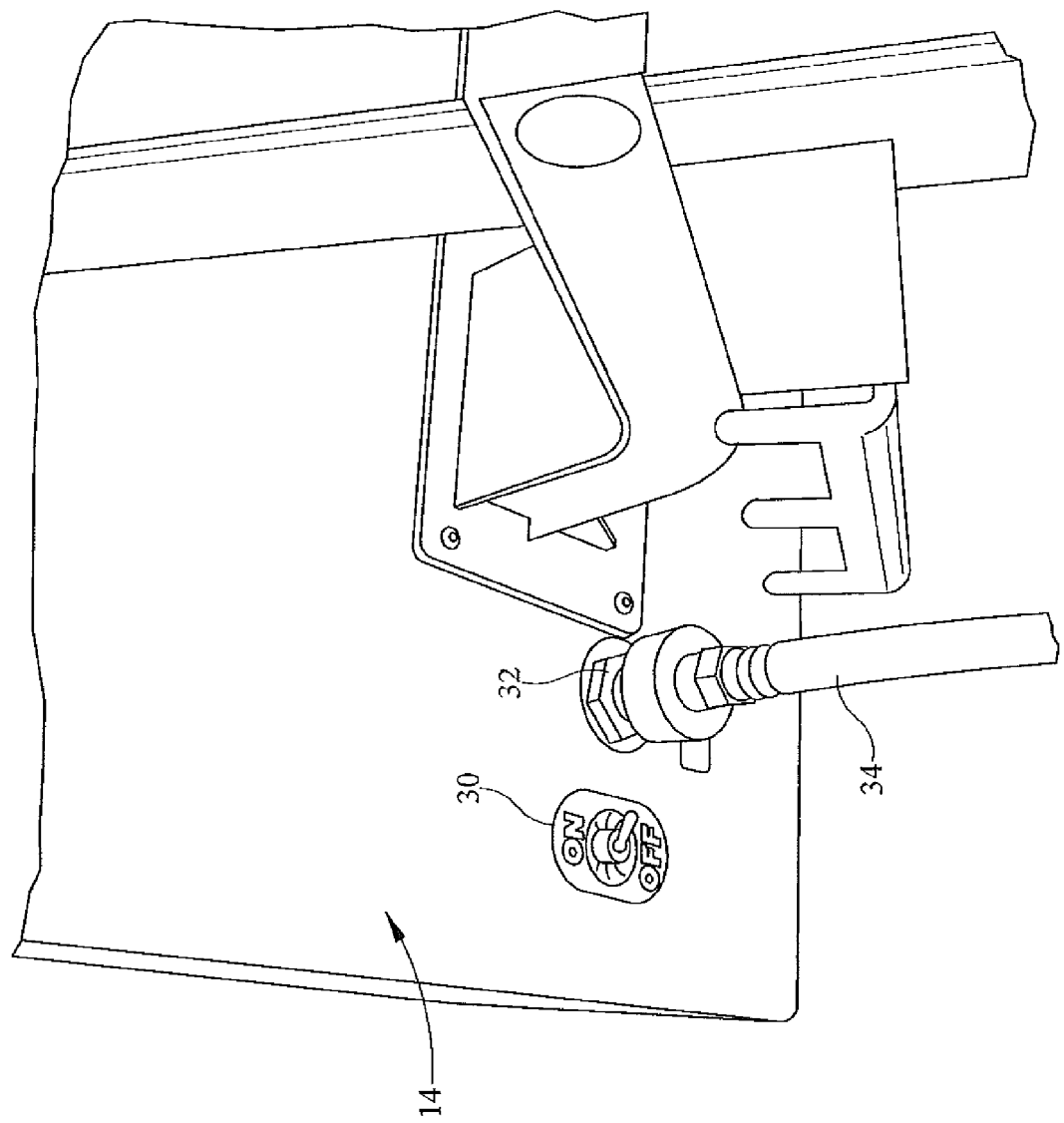

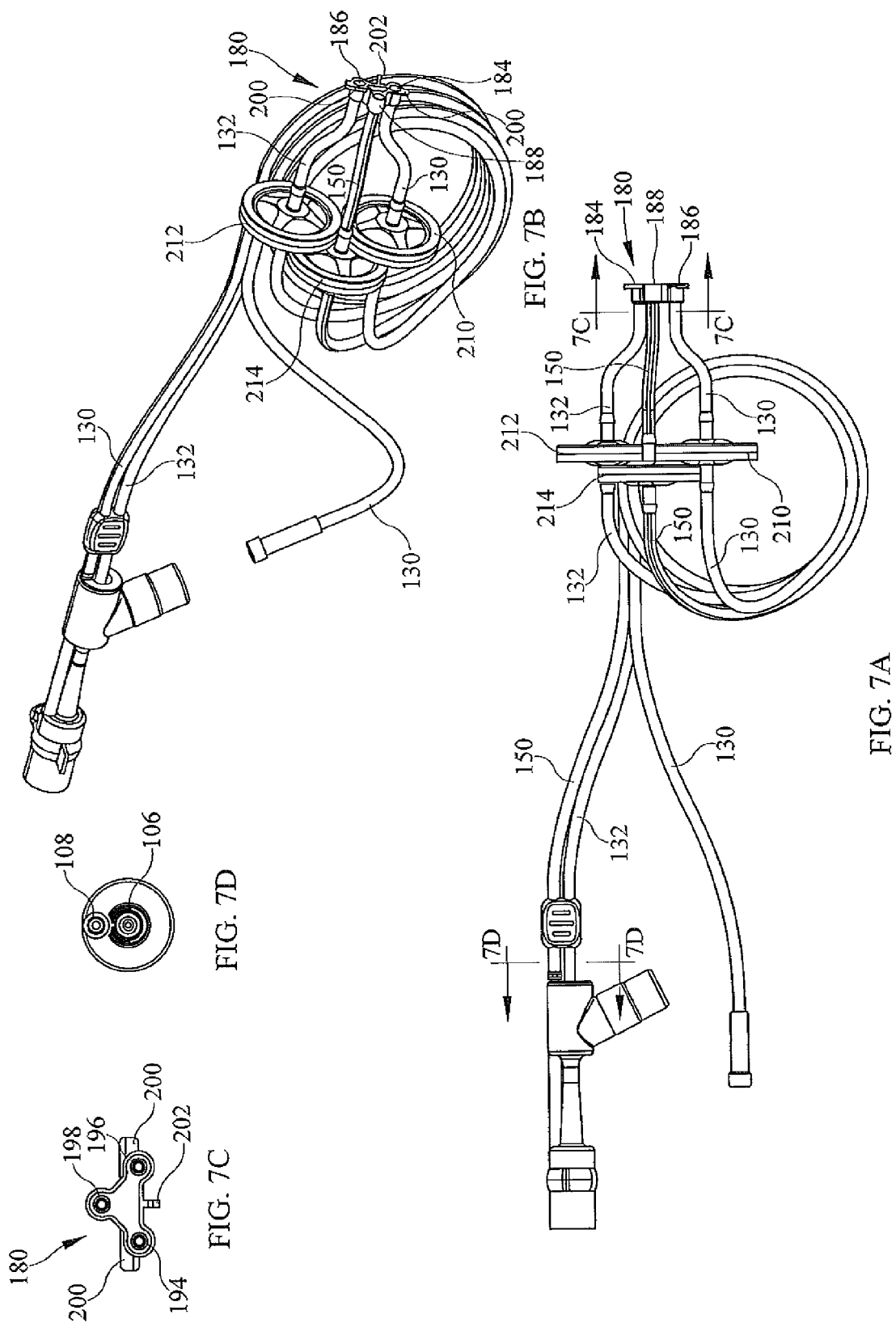

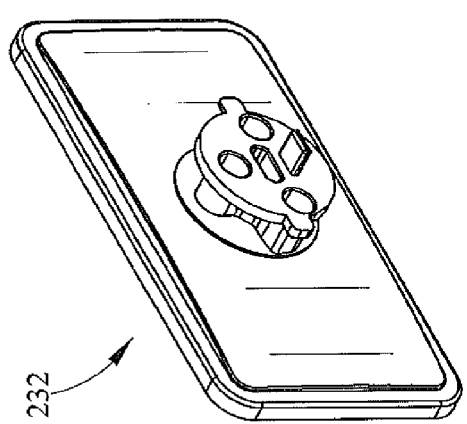
FIG. 9D
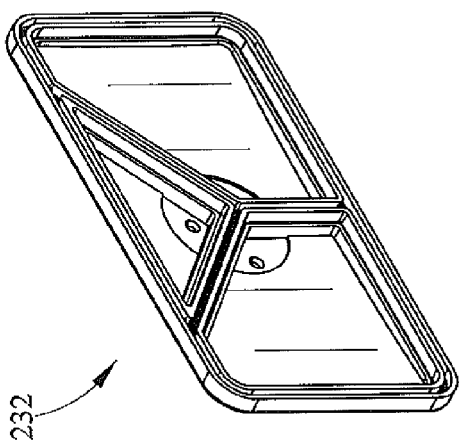
FIG. 9E
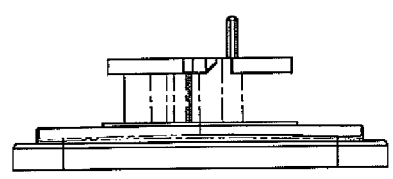
FIG. 9C
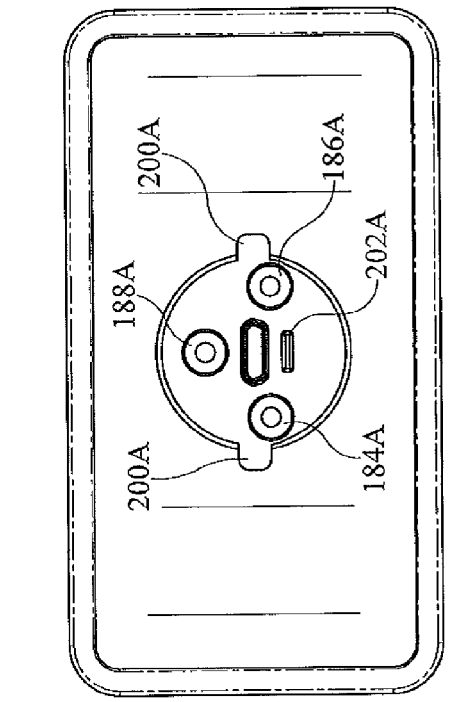
FIG. 9A
FIG. 9B

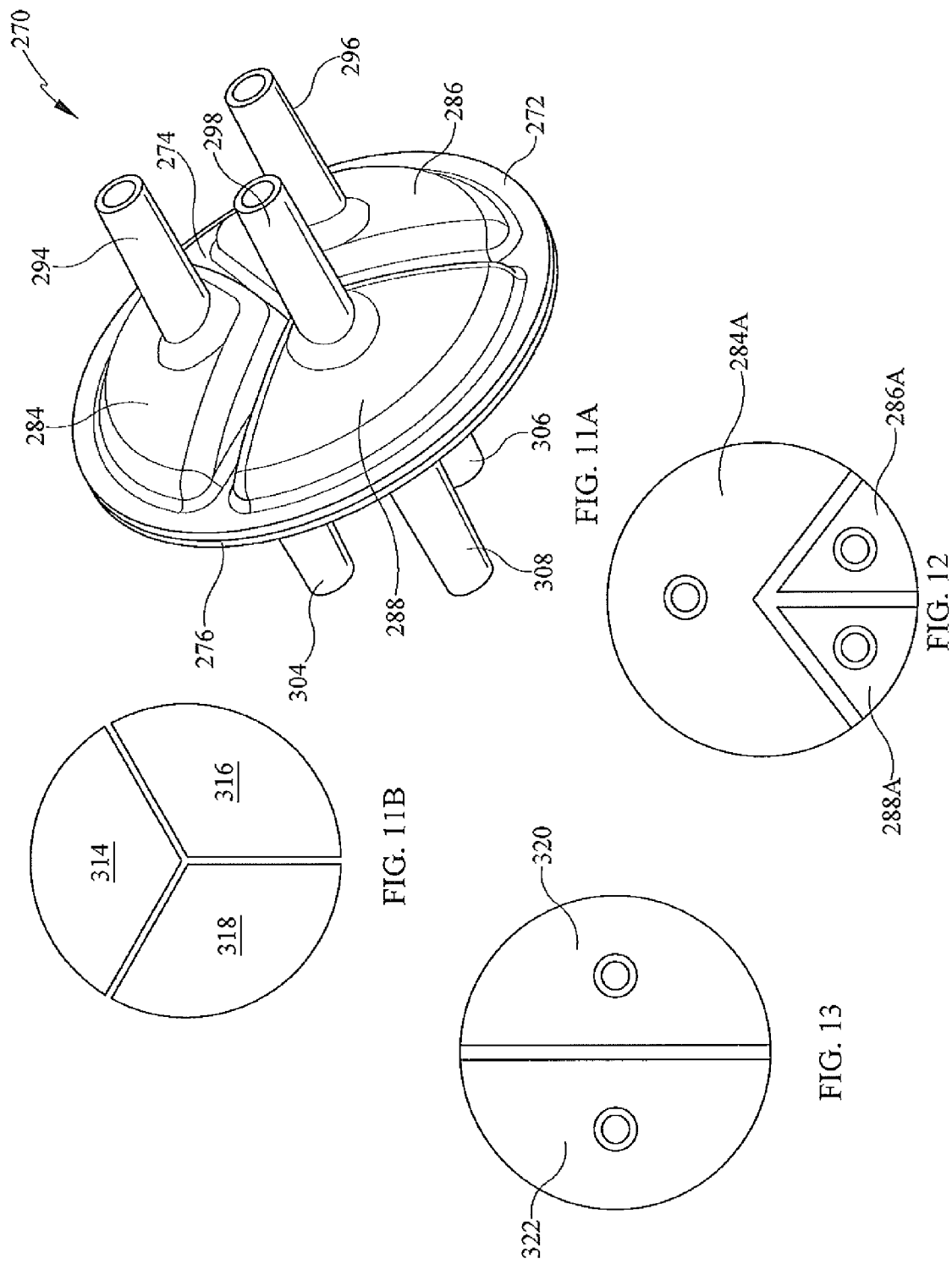

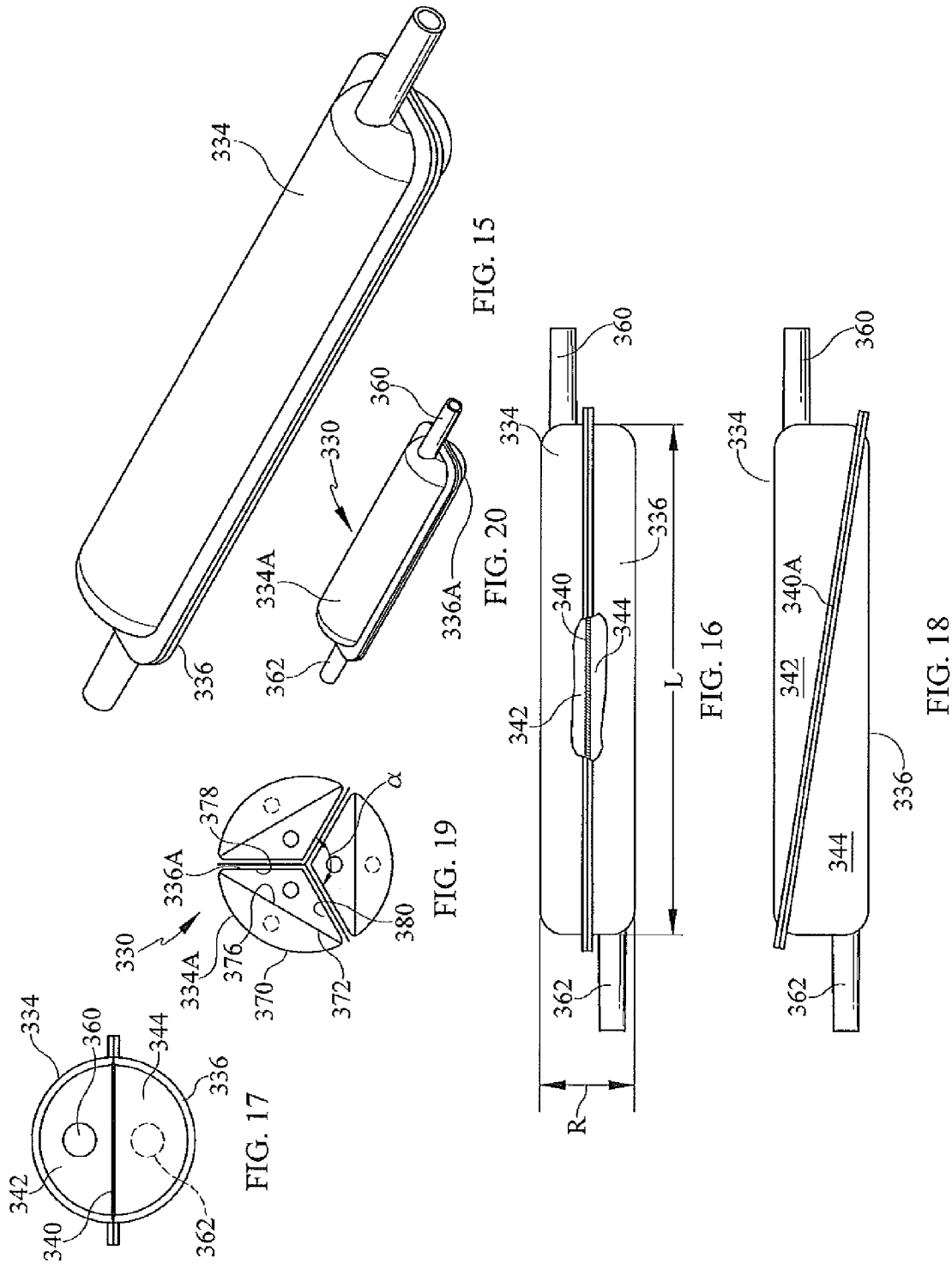

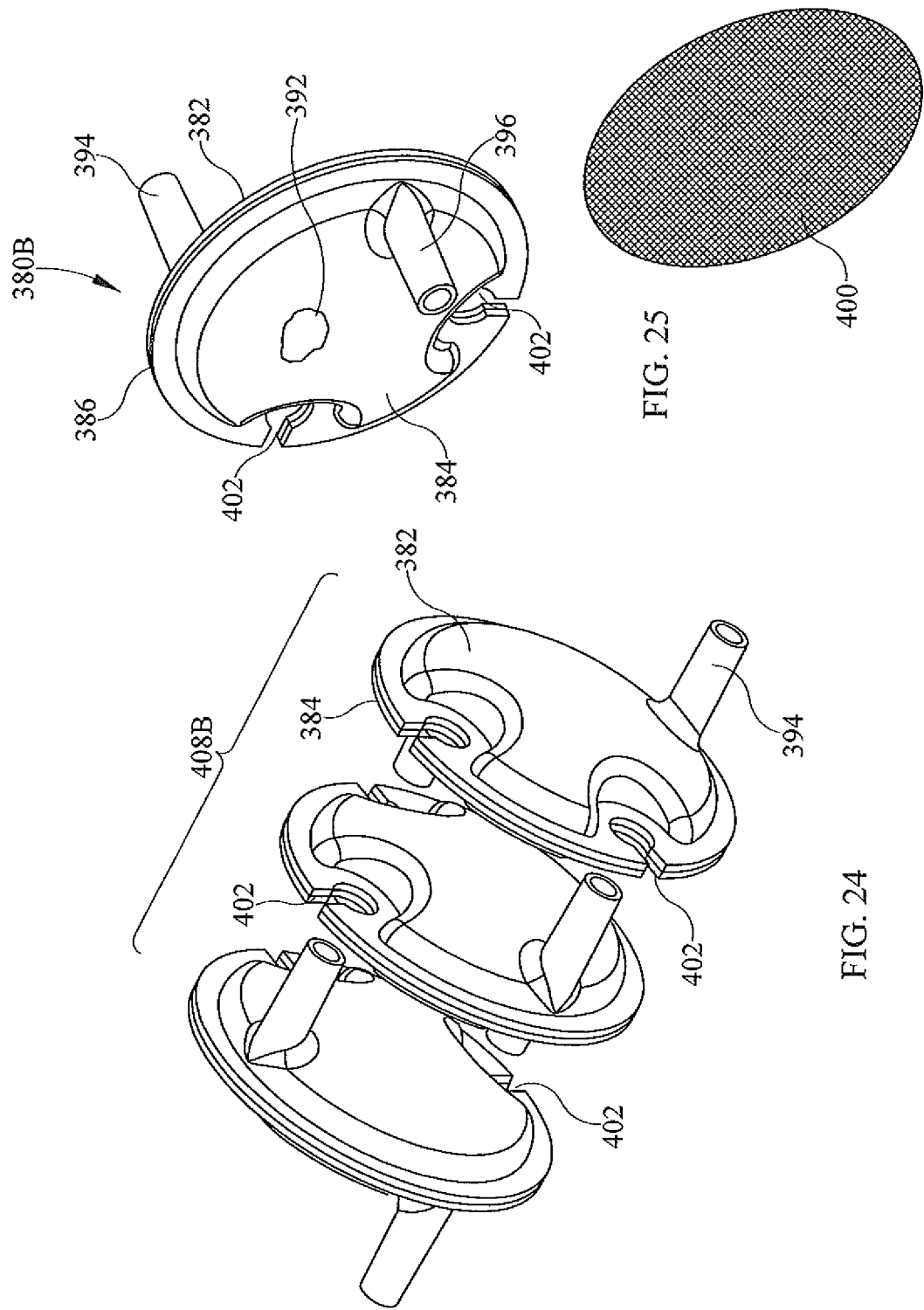

FILTRATION UNIT USEABLE IN A RESPIRATORY THERAPY DEVICE

TECHNICAL FIELD

The subject matter described herein relates to a respiratory therapy device having a gas filter and to filtration modules, units assemblies and subassemblies for use with such respiratory therapy devices. This application is a divisional of U.S. patent application Ser. No. 13/685,103 (now U.S. Pat. No. 9,272,115) entitled "Respiratory Therapy Device and Filtration Units Therefor" filed on Nov. 26, 2012, the contents of which are incorporated herein by reference.

BACKGROUND

Respiratory therapists may rely on various items of equipment to apply respiratory therapy to a patient. One particular respiratory therapy device delivers a medicated aerosol to a patient or applies a composite therapy involving alternation between continuous high frequency oscillation (CHFO) therapy and continuous positive expiratory pressure (CPEP) therapy each in conjunction with aerosol delivery. All three modes of operation (aerosol, CHFO, CPEP) involve some risk of cross contamination, i.e. contamination of the patient by a gas stream delivered by the therapy device, or contamination of nondisposable components of the device by the patient. Accordingly, it is desirable to develop ways to reduce the risk of cross contamination.

SUMMARY

A respiratory therapy device comprises a pneumatic control unit connectable to a source of medical grade oxygen. The control unit is adapted to supply medical grade oxygen to a first control unit outlet port at a first set of conditions and to a second control unit outlet port at a second set of conditions. The device also includes a first transfer conduit in fluid communication with the first outlet port and a second transfer conduit in fluid communication with the second outlet port. The first transfer conduit defines at least part of a first flowpath to a first destination. The first flowpath includes a first filter. The second transfer conduit defines at least part of a second flowpath to a second destination. The second flowpath includes a second filter. A related filtration module comprises a filter housing defining two or more filter compartments. The housing has an input side with a gas inlet in fluid communication with each of the filter compartments and a gas outlet in fluid communication with each of the filter compartments. A filter element resides in each of the compartments intermediate the gas inlet to the compartment and the gas outlet from the compartment.

BRIEF DESCRIPTION OF THE DRAWINGS

The foregoing and other features of the various embodiments of the respiratory therapy device and filtration devices described herein will become more apparent from the following detailed description and the accompanying drawings in which:

FIG. 1E is a view of a portion of the back side of the therapy unit of FIGS. 1A through 1D.

FIGS. 7A and 7B are a side elevation view and a perspective view respectively of the respiratory therapy device showing in-line filters in the transfer conduits and pressure sensor line of the therapy device.

FIGS. 7C and 7D are views in the direction 7C-7C and 7D-7D of FIG. 7A.

FIGS. 9A and 9B are plan views of the interior side and exterior side of an inlet shell of the filter module of FIG. 8.

FIG. 9C is a side elevation view of the inlet shell of FIGS. 9A and 9B

FIGS. 9D and 9E are perspective views of the exterior side and interior side of the inlet shells of FIGS. 9A and 9B.

FIG. 11A is a perspective view of a substantially circular filter module having three filter compartments that are equally sized sectors of a circle.

FIG. 11B is a schematic view of the filter compartment arrangement in the interior of the filter module of FIG. 11A.

FIGS. 12-13 are views of a circular filter module similar to that of FIG. 11 having alternative filter compartment configurations.

FIG. 15 is a perspective view of one of the subassemblies of FIG. 14.

FIG. 16 is a side elevation view of the filter subassembly of FIG. 15 with a portion broken away to reveal a filter element and associated compartments on the inlet and outlet sided of the filter element.

FIG. 17 is a cross sectional end elevation view of the filter subassembly of FIGS. 15 and 16.

FIG. 18 is a cross section of a subassembly similar to that of FIG. 16 but with an obliquely oriented filter element.

FIGS. 19-20 are an end cross sectional view and a perspective view of another embodiment of a filter subassembly comprised of two shells, one of which has a cross section defined by a curved line segment and a straight line segment connecting the ends of the curved segment and the other of which has a cross section defined by three straight or approximately straight line segments.

FIG. 24 is an exploded perspective view and an exploded cross sectional side elevation view of a second variant of a filter assembly comprised of multiple filter units arranged in tandem, each filter unit being comprised of an inlet shell and an outlet shell.

FIG. 25 is a perspective view of one of the filter units of FIG. 24

DETAILED DESCRIPTION

Figure 1A:
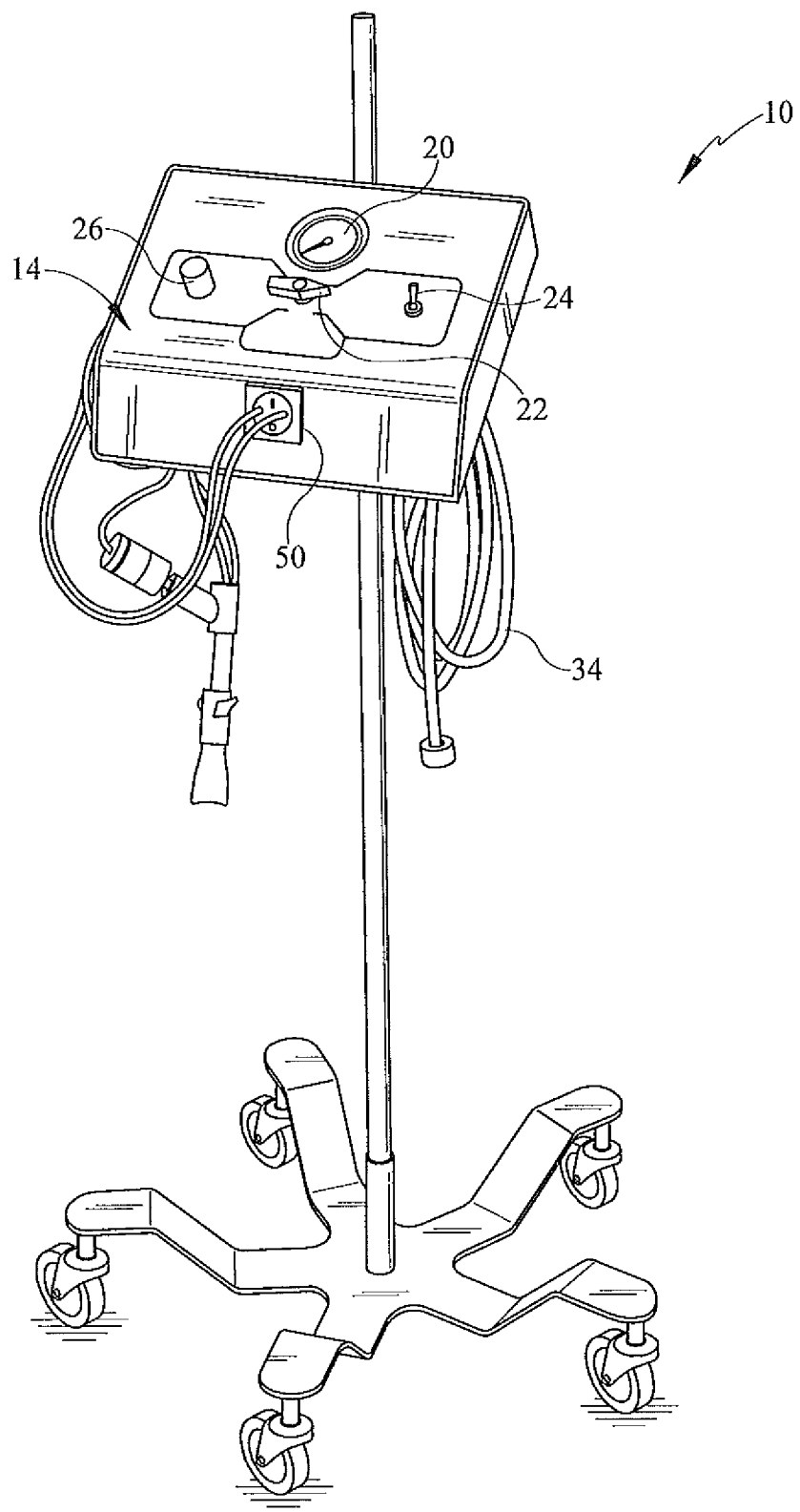
FIGS. 1A, 1B 1C and 1D are views of the front side of a respiratory therapy device for delivering an aerosol to a patient or for applying a composite therapy involving alternation between continuous high frequency oscillation (CHFO) therapy and continuous positive expiratory pressure (CPEP) therapy, each in conjunction with aerosol delivery.
Figure 1B:
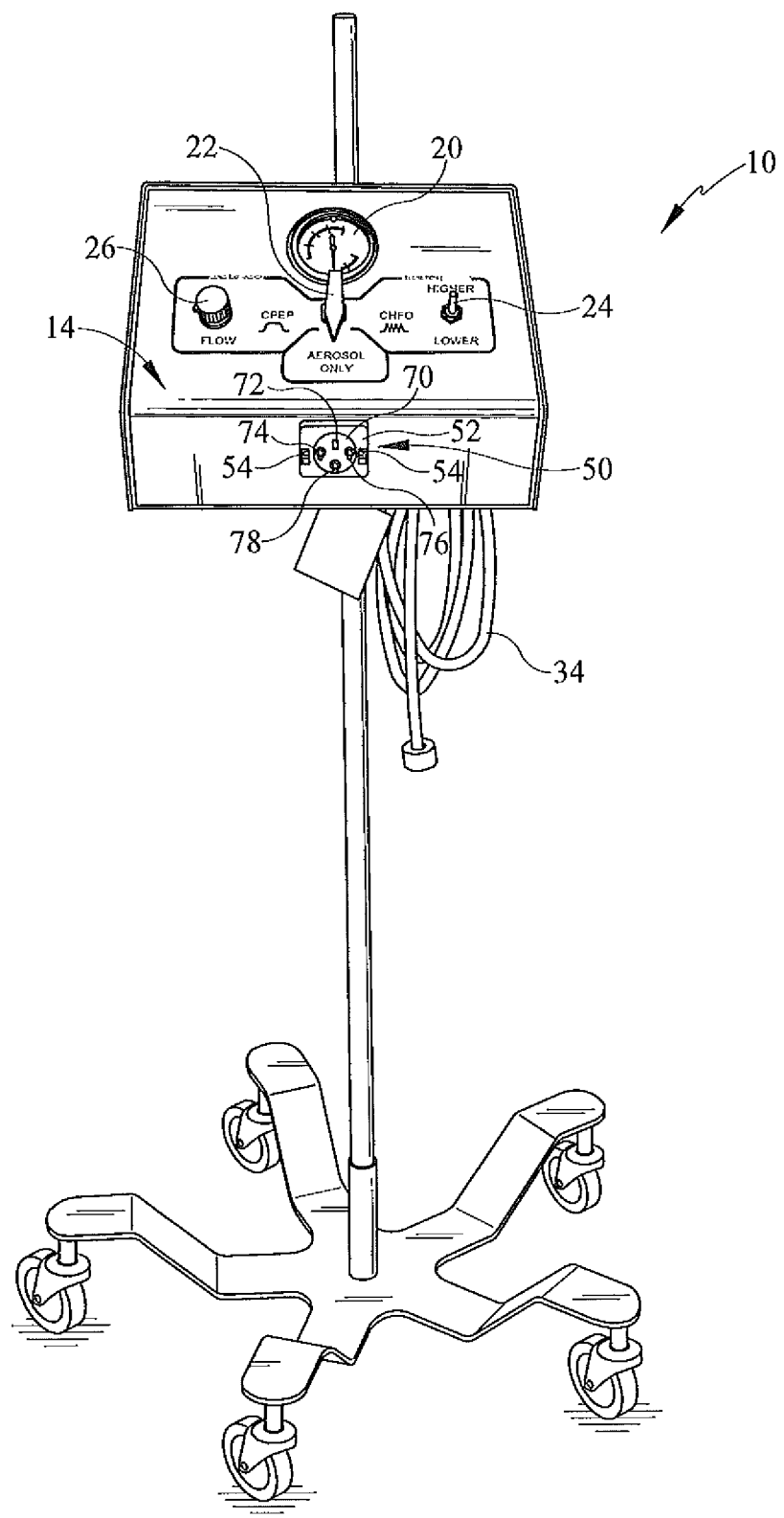

FIGS. 1A through 1E and 2-4 show a respiratory therapy device 10. The device is used by a respiratory therapist to deliver a medicated aerosol to a patient or to apply a composite therapy involving alternation between continuous high frequency oscillation (CHFO) therapy and continuous positive expiratory pressure (CPEP) therapy each in conjunction with aerosol delivery. The device includes a pneumatic control unit 12 (FIGS. 2-4) housed inside a cabinet or housing 14. The components of the device that are normally visible from the front side of the cabinet include a manometer 20, a mode selector switch 22 for selecting among "aerosol only", CPEP and CFHO therapies, a percussive intensity switch 24 for selecting between a higher percussion rate and pressure and a lower percussion rate and pressure when the unit is operated in the CHFO mode, and a flow regulation knob 26 enabling a user to adjust gas flow rate when the unit is operated in the CPEP mode. The components of the device that are normally visible from the back side of the cabinet include a master ON/OFF switch 30 and an oxygen gas connector 32 for connecting the control unit to a source of medical grade oxygen, for example by way of an oxygen supply hose 34 connected to an oxygen gas outlet in the wall of a medical facility.

The therapy unit also includes a male quick disconnect assembly 50 comprising a base 52 with a pair of retainers 54. Each retainer has a face 60 spaced from the base by a flank 62. The right retainer includes a stop 64 at its upper extremity and an opening 66 (not visible) at its lower extremity. The left retainer includes a stop 64 at its lower extremity and an opening 66 at its upper extremity. The male quick disconnect assembly also includes a connector disk 70 having a receptacle 72, first and second male outlet ports 74, 76 and a third male port 78. The third port is a pressure sense port. Unlike first and second ports 74, 76 which accommodate fluid (oxygen) flow, the pressure sense port is part of a pressure sensing system. Accordingly, during operation of the device there is no steady state macroscopic fluid transport through third port 78. Nevertheless, port 78 is sometimes referred to as an outlet port due to its physical proximity to true outlet ports 74, 76 rather than as an indication of its function.

Figure 1C:
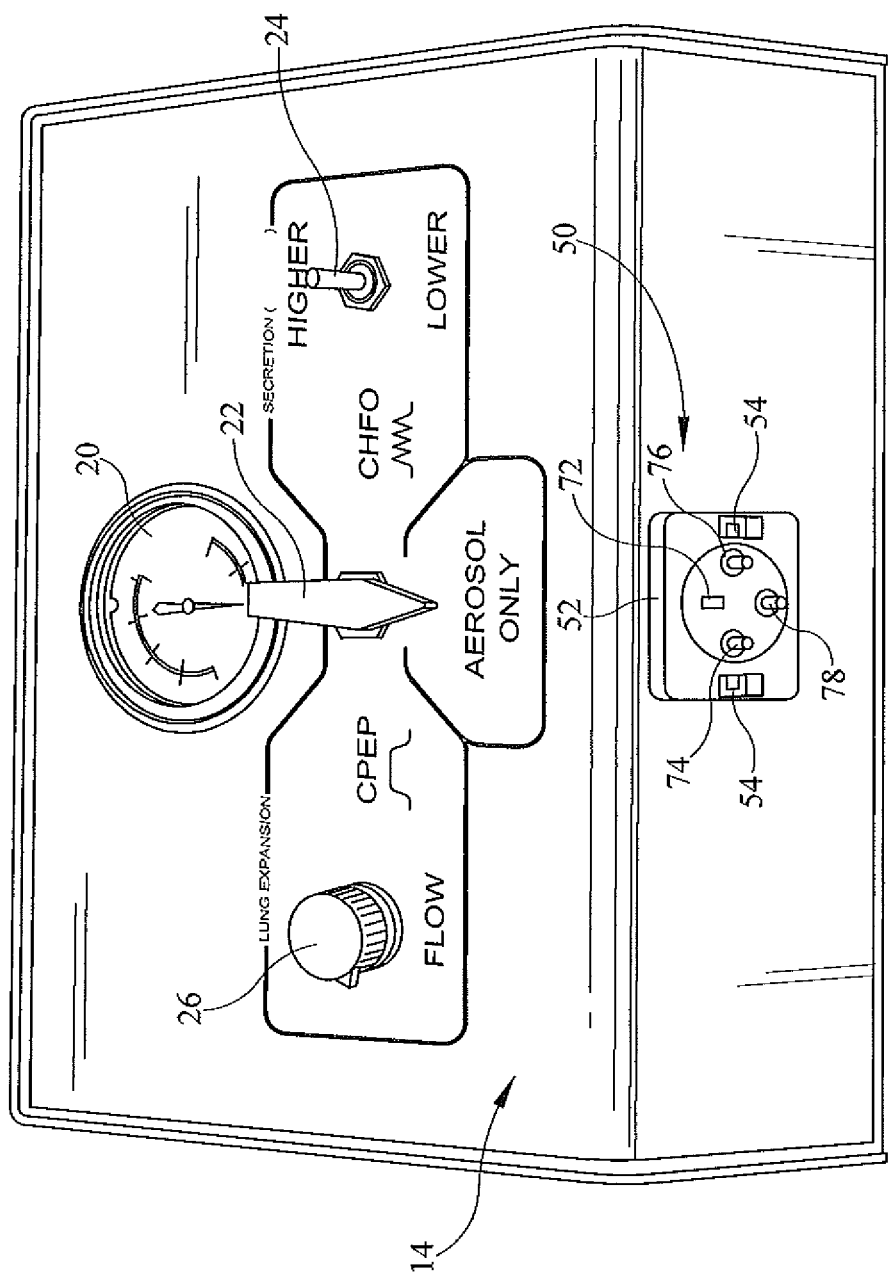
Figure 1D:
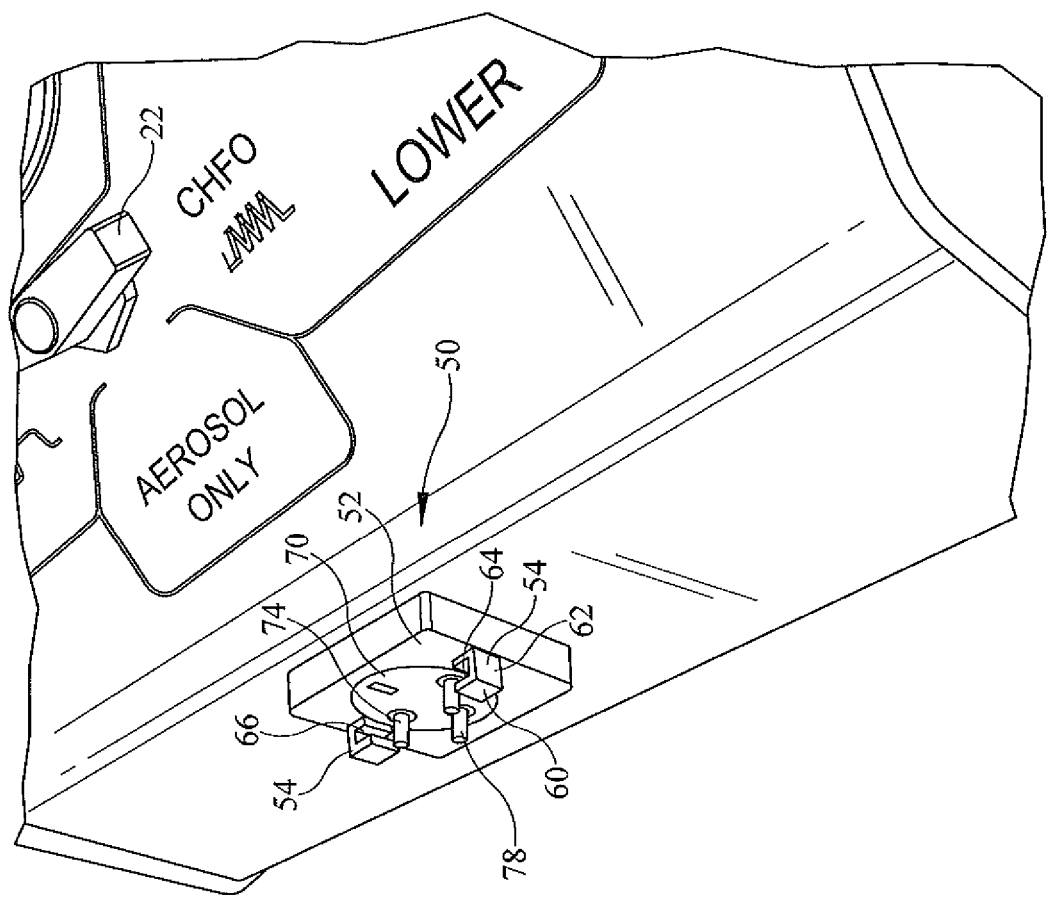

Connector disk 70 is rotatable through an angle of about 45 degrees between a "connect" orientation (FIG. 1E) and an "operational" orientation (e.g. FIG. 1C). In the "connect" orientation ports 74, 76, 78 of the connector disk can receive (or be disengaged from) a correctly designed, counterpart female connector, however ports 74, 76, 78 are not aligned with source tubes 84, 86, 88 seen in FIGS. 2-3. In the "operational" orientation ports 74, 76, 78 of the connector disk cannot receive (or be disengaged from) the correctly designed counterpart female connector, however ports 74, 76, 78 are aligned with source tubes 84, 86, 88.

Figure 5:
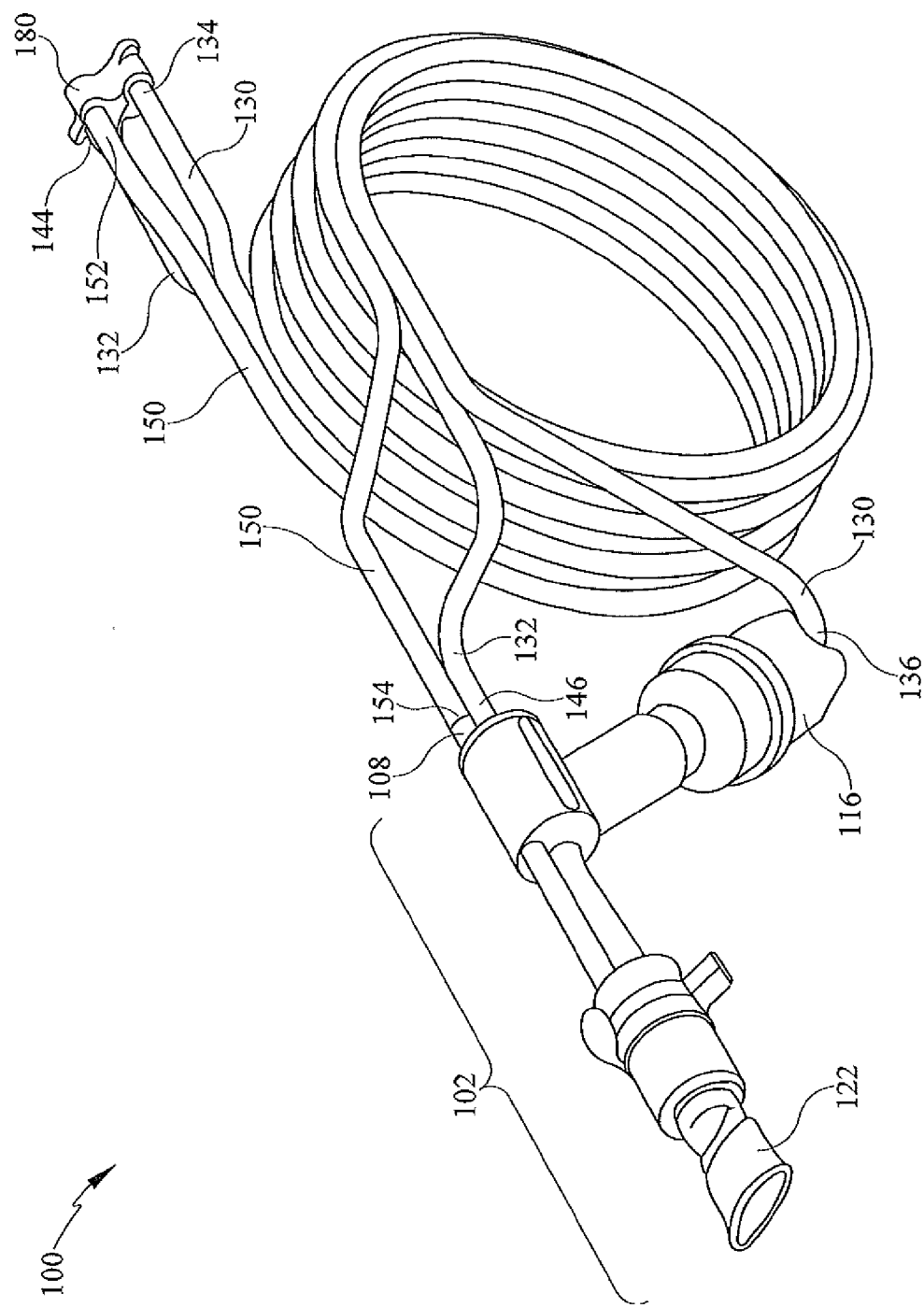
FIG. 5 is a perspective view of a circuit component of the therapy device.
Figure 6:
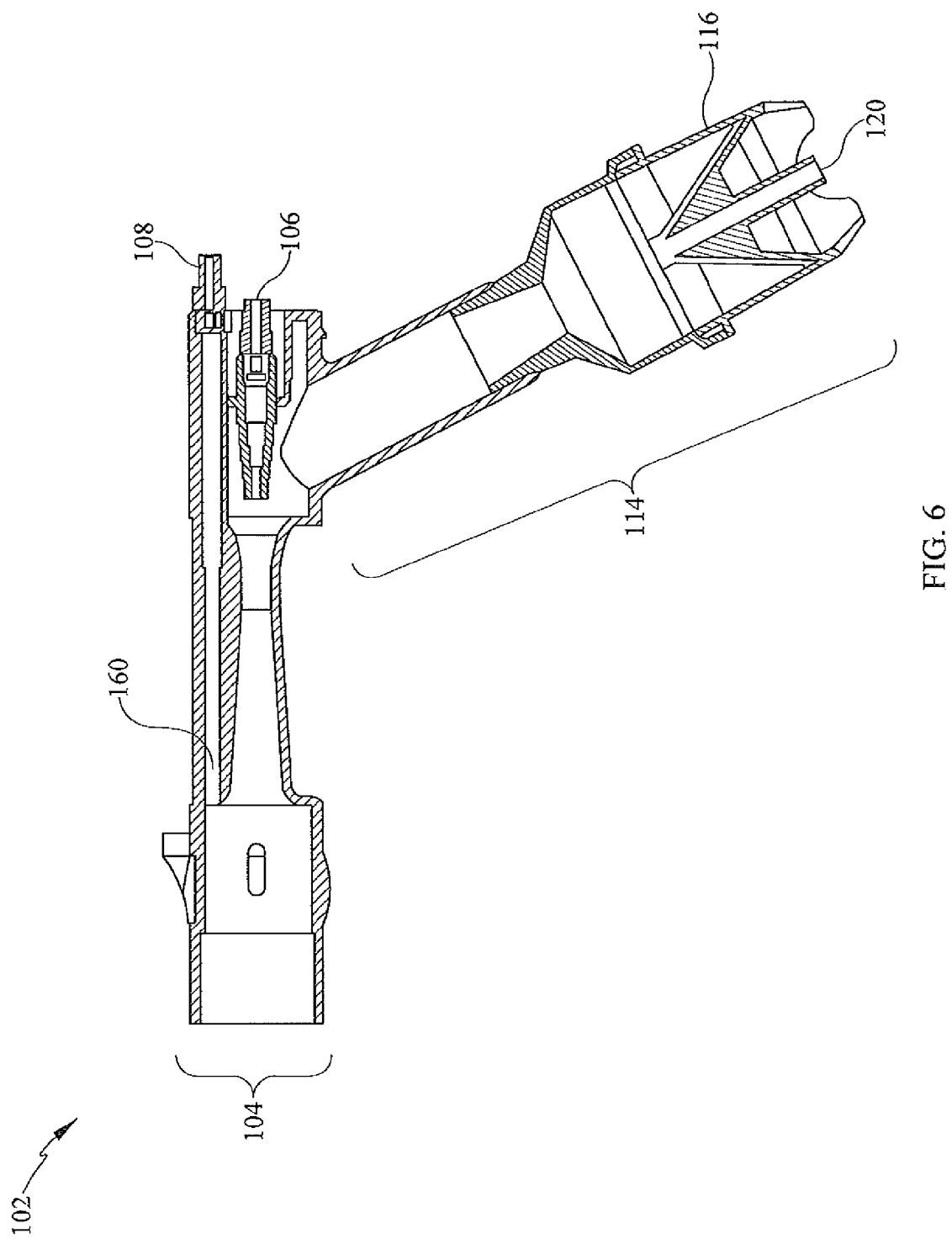
FIG. 6 is a cross sectional side elevation view of a handset component of the circuit of FIG. 5.

Referring to FIGS. 5-6 the therapy device also includes a component referred to as a circuit 100. The circuit includes a handset 102. The handset includes a main body portion 104 having a therapy gas connector 106 and a pressure sense connector 108. The handset also includes a nebulizer branch 114 having a nebulizer canister 116 with a nebulizer connector 120. A patient mouthpiece 122 is connectable to the end of the main body remote from connectors 106, 108. The therapy device also includes first and second transfer conduits 130, 132. The first transfer conduit has a control unit terminus 134 and a handset terminus 136. Terminus 134 is intended to be in communication with first control unit outlet port 74; terminus 136 is connected to nebulizer connector 120. The first transfer conduit defines at least part of a first flowpath extending at least from first control unit outlet port 74 to a first destination. In the illustrated example the first destination is nebulizer connector 120. Second transfer conduit 132 also has a control unit terminus 144 and a handset terminus 146. Terminus 144 is intended to be in communication with second control unit outlet port 76; terminus 146 is connected to therapy gas connector 106. The second transfer conduit defines at least part of a second flowpath extending at least from second control unit outlet port 76 to a second destination. In the illustrated example the second destination is therapy gas connector 106.

The therapy device also includes a pressure sense line 150 having a control unit terminus 152 and a pressure pickup terminus 154. Terminus 152 is intended to be in communication with third control unit port 78 (i.e. pressure sense port 78); terminus 154 is connected to pressure sense connector 108. The pressure sense line defines at least part of a third path, also referred to as a pressure sense path, extending at least from third control unit port 78 to pressure sense connector 108. As a practical matter the third path extends from manometer 20 to a location 160 in handset 102 where gas pressure is representative of a pressure to be monitored.

Figure 2:
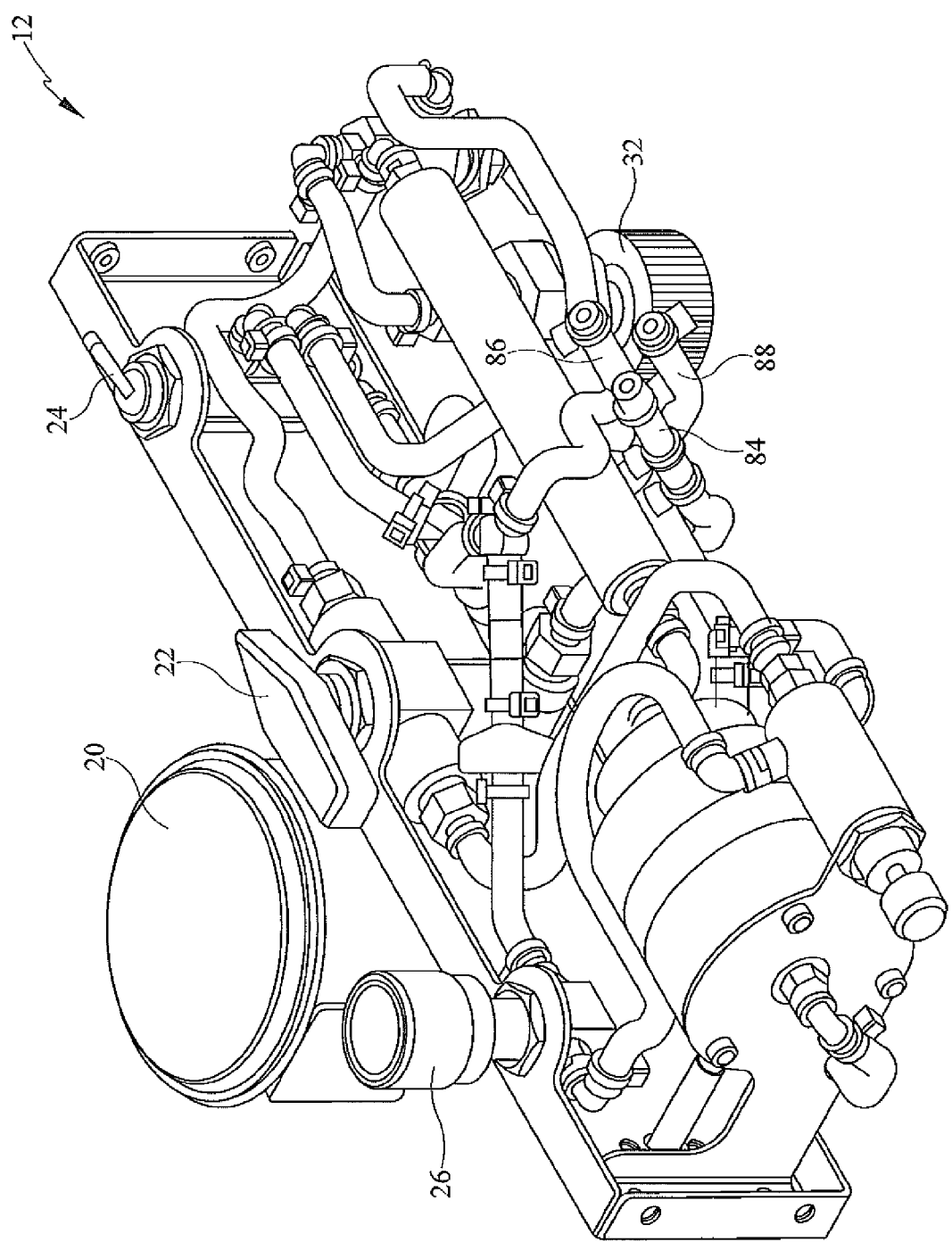
FIGS. 2 and 3 are a perspective view and a front elevation view respectively of pneumatic controller hardware for the therapy device.
Figure 3:
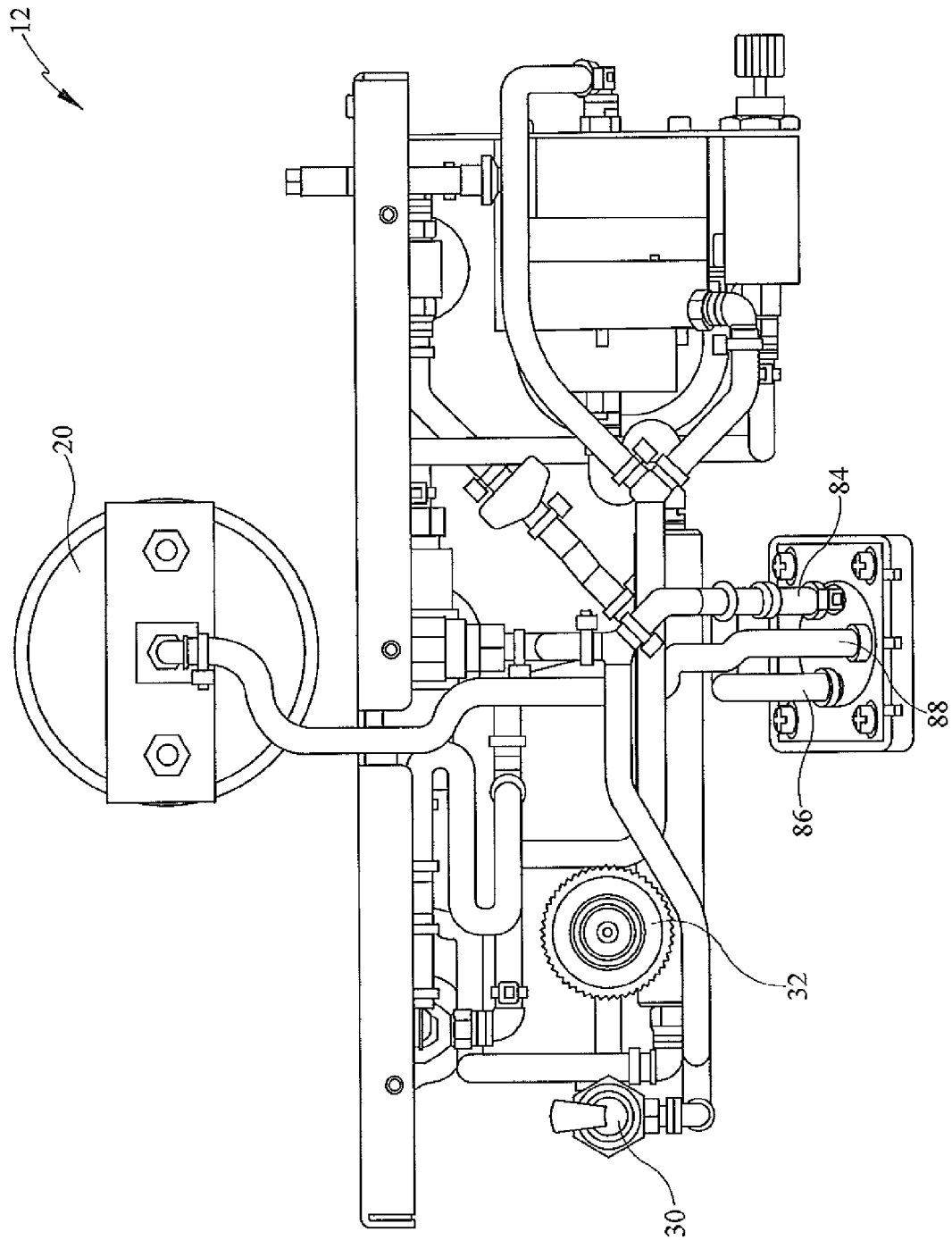
Figure 4:
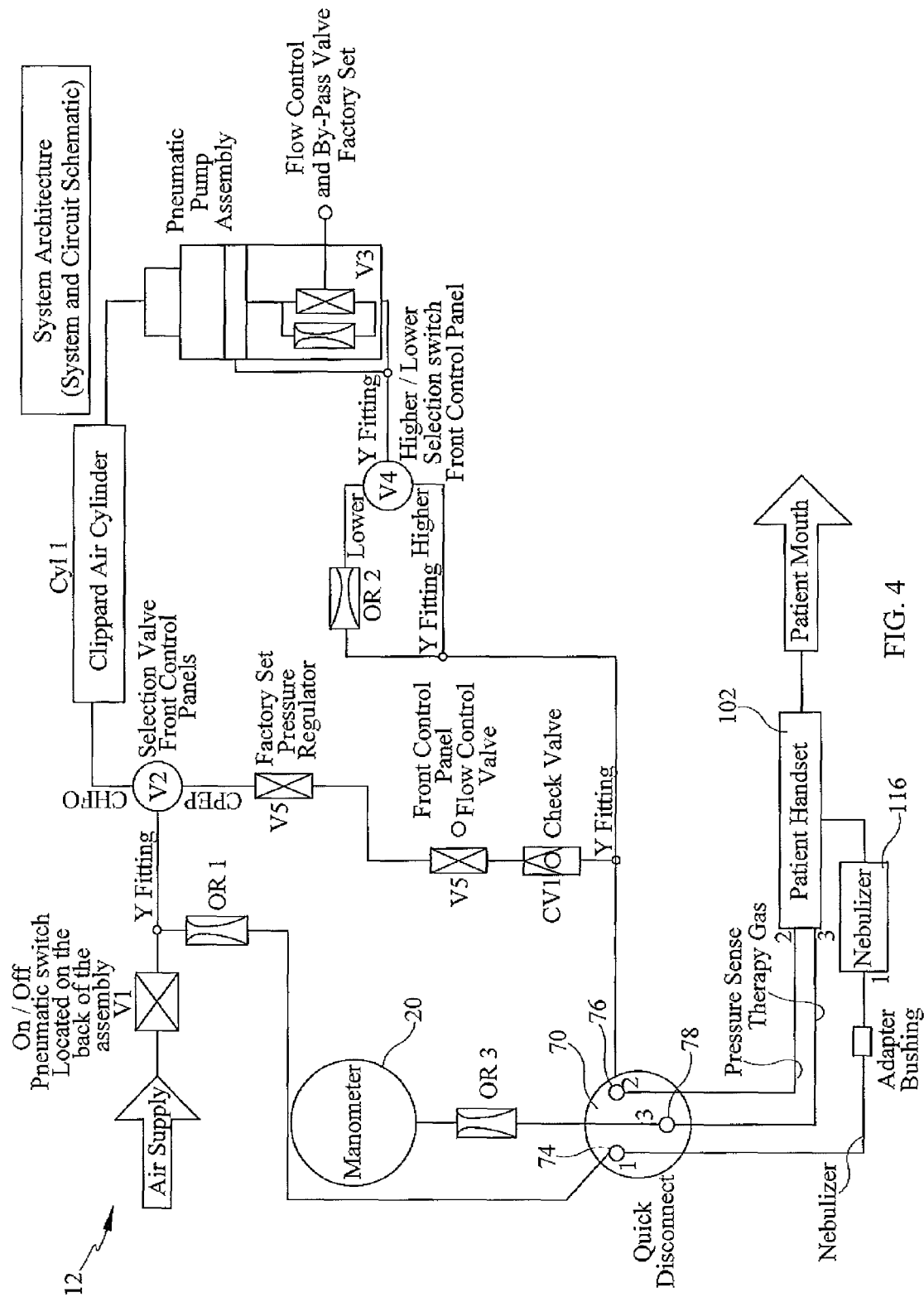
FIG. 4 is a schematic of the pneumatic controller of FIGS. 2 and 3.
Figure 7G:
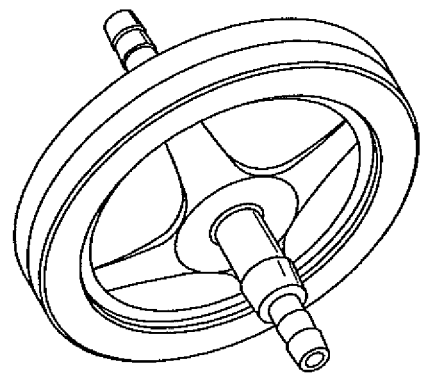
FIGS. 7E, 7F and 7G are a side elevation view, end elevation view and a perspective view respectively of a representative in-line filter of FIGS. 7A and 7B.
Figure 7F:
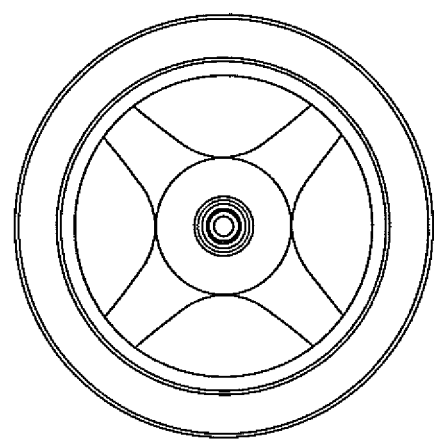
Figure 7E:
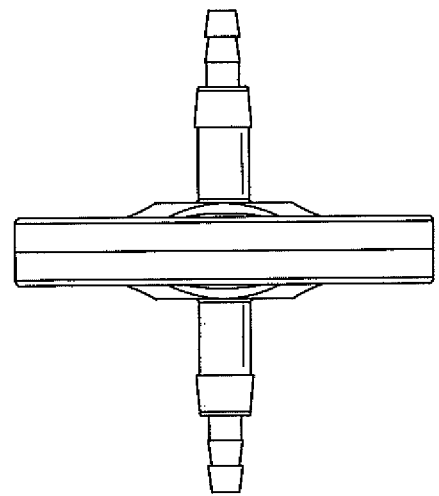

Referring additionally to FIGS. 7A, 7B, 7C, circuit 100 also includes a connector unit 180 which is also referred to as a tri-connector. Connector unit 180 has a female side with first, second and third inlets 184, 186, 188 clustered together in a single unit, and a male side with first, second and third outlets 194, 196, 198, each in the form of a serrated or barbed projection. Connector unit 180 also includes a pair of radially projecting tabs 200 and a key in the form of a prong 202 that projects past the plane of inlets 184, 186, 188. When a user wishes to connect circuit 100 to control unit 12, the user ensures that connector disk 70 is in its "connect" orientation (FIG. 1D) and then pushes the female side of connector unit 180 (with transfer conduits 130, 132 and pressure sense line 150 preferably already connected to outlet projections 194, 196, 198) onto control unit outlet ports 74, 76, 78. At the same time, prong 202 enters receptacle 72 of connector disk 70. The user then rotates connector unit 180 counterclockwise (as seen from the perspective of FIGS. 1A through 1C) which causes connector disk 70 to also rotate and tabs 200 to slide through retainer openings 66, until the tabs encounter stops 64. The connector unit tabs are thus trapped behind retainer faces 60 so that the retainers resist unintended disconnection of connector unit 180 from the pneumatic control unit and so that outlet ports 74, 76, 78 are correctly aligned with tubes 84, 86, 88 (FIGS. 2-3). Because inlets 184, 186, 188 are all part of a single connector unit, the inlets are connectable in unison to the control unit so that each inlet registers with a prescribed port 74, 76, 78 of the therapy device control unit. Prong 202 and receptacle 72 are in a common orientation so that receptacle 72 will receive the prong and so that connector unit inlets 184, 186, 188 will receive connector disk outlet ports 74, 76, 78 only if the user is making a connection between a mutually compatible circuit and control unit. A circuit and a control unit that are incompatible with each other will have a prong and a receptacle oriented sufficiently differently that a proper connection cannot be made. Accordingly, the prong and receptacle constitute an error proofing feature.

Control unit 12 is adapted to supply medical grade oxygen to first control unit outlet port 74, which can also be referred to as a nebulizer outlet port, at a first set of conditions. The first conditions include pressure and flow rate consistent with the needs of the nebulizer. Control unit 12 is also adapted to supply the medical grade oxygen to second control unit outlet port 76, which can also be referred to as a therapy gas outlet port, at a second set of conditions. The second conditions include pressure, flow rate consistent with the desired intensity of CPEP therapy and pressure, flow rate, percussive frequency and percussive amplitude consistent with the desired intensity of CHFO therapy.

Referring now to FIGS. 7A through 7G, The respiratory therapy device includes a first filter 210 located in a portion of the first flowpath defined by first transfer conduit 130 and a second filter 212 located in a portion of the second flowpath defined by second transfer conduit 132. The device also includes a third filter 214 located in a portion of the pressure sense path defined by pressure sense line 150. The filters are referred to as in-line filters due to their location between the terminii of the transfer conduit or pressure sense line. The filter is an off the shelf filter. The filters in the transfer conduits help reduce the possibility of cross contamination, i.e. contamination of the patient due to impurities that might be present in the oxygen gas supply (even though medical grade oxygen should be substantially free of contaminants) and/or contamination of the control unit by the patient. The filter in the pressure sense line similarly guards against cross contamination, but because the pressure sense line carries static fluid rather than flowing fluid, the pressure sense line is less likely to be a conveyor of contaminants. Therefore, the filter in the pressure sense line is more precautionary than the other filters.

Figure 8:
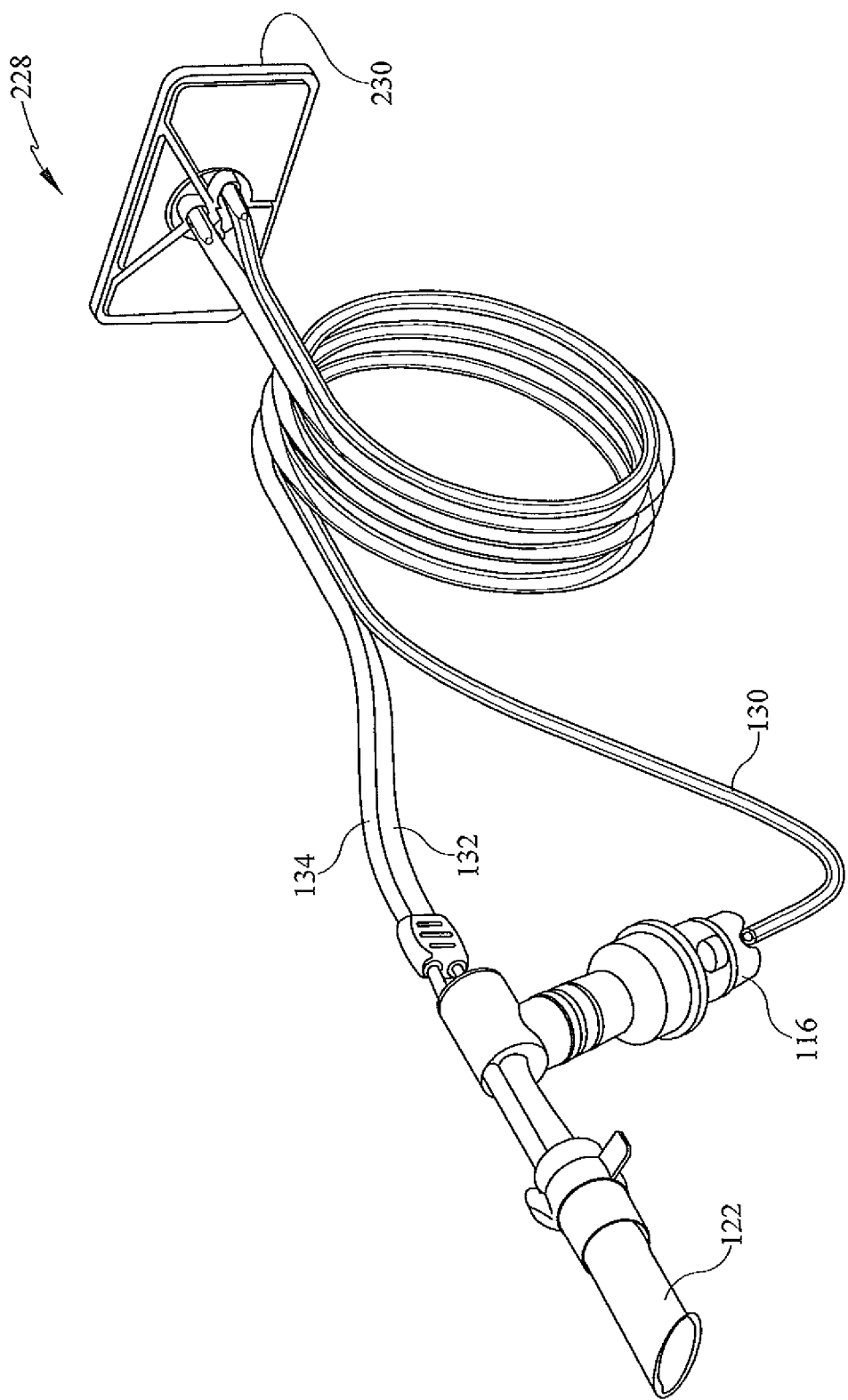
FIG. 8 is a perspective view of a circuit having a non-in-line filtration module as seen from an output side of the module.
Figure 9H:
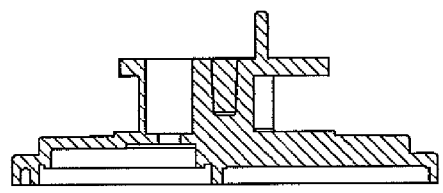
FIG. 9H is a cross sectional side elevation view taken along 9H-9H of FIG. 9F.
Figure 9I:
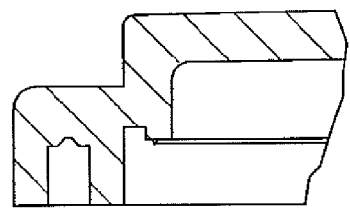
FIG. 9I is a detail of FIG. 9H.
Figure 9F:
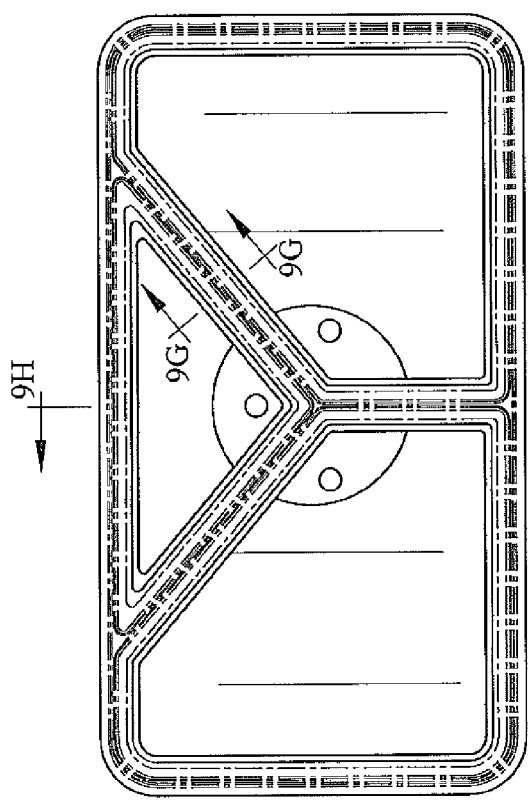
FIG. 9F is a plan view similar to that of FIG. 9A.
Figure 9G:
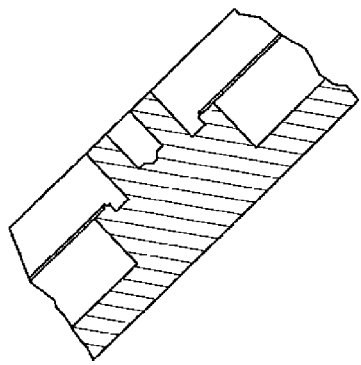
FIG. 9G is a cross section taken along 9G-9G of FIG. 9F.
Figure 9M:
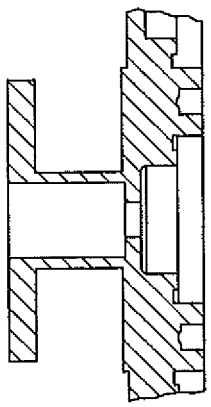
FIG. 9M is a cross section taken along 9M-9M of FIG. 9J.
Figure 9J:
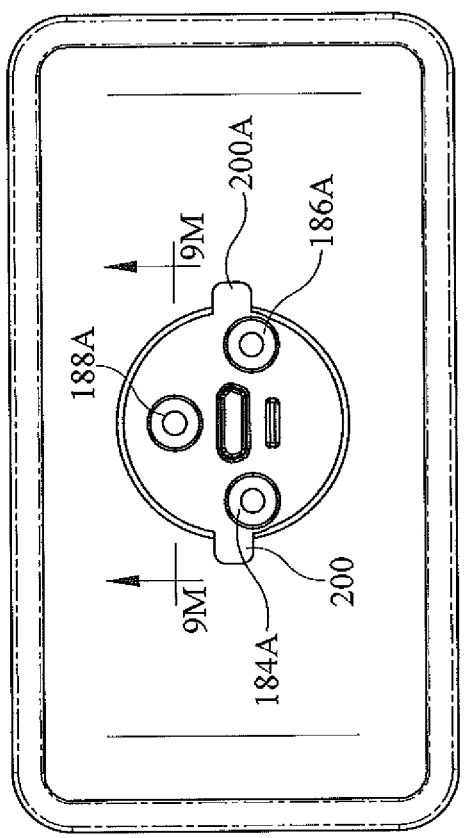
FIG. 9J is a plan view similar to that of FIG. 9B.
Figure 9L:
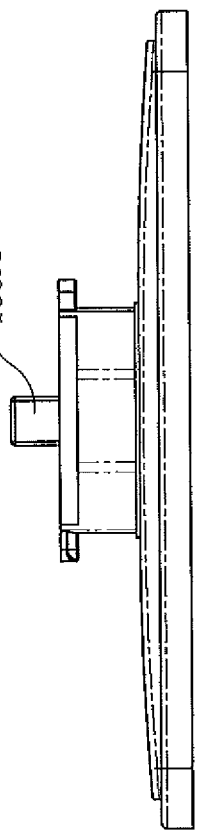
FIGS. 9K and 9L are a side elevation view and a bottom view of the shell of FIG. 9J.
Figure 9K:
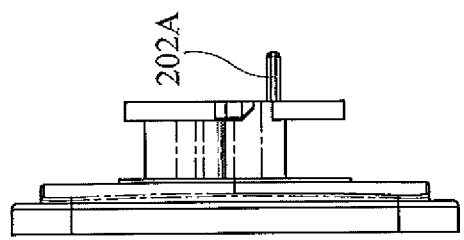
Figure 10D:
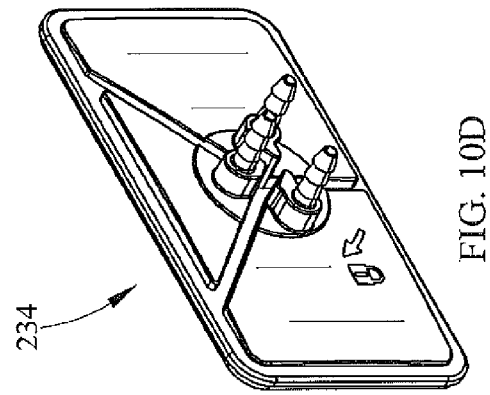
FIGS. 10A through 10M are views analogous to those of FIGS. 9A through 9M but showing an outlet shell of the filter housing of FIG. 8.
Figure 10E:
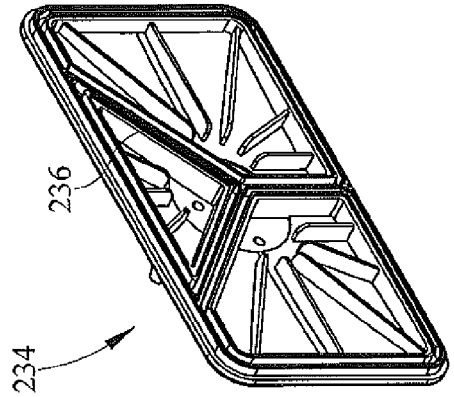
Figure 10C:
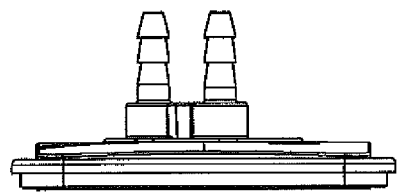
Figure 10A:
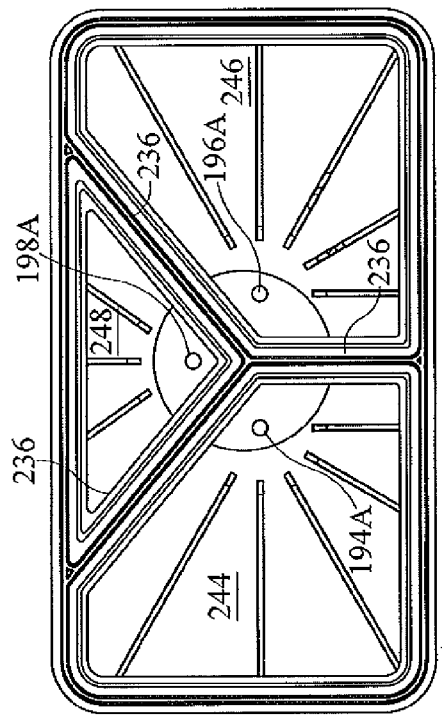
Figure 10B:
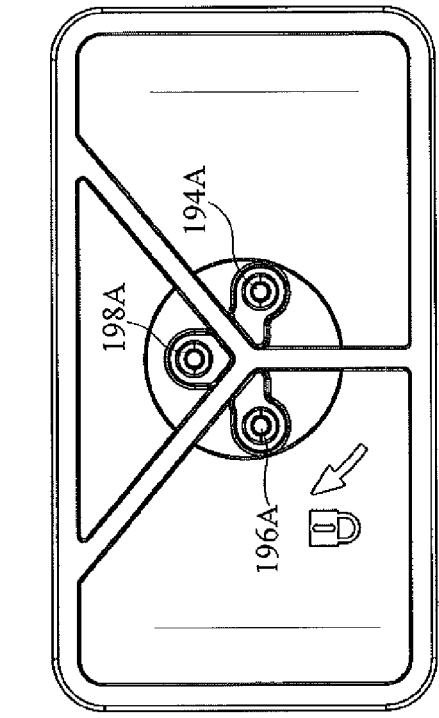
Figure 10H:
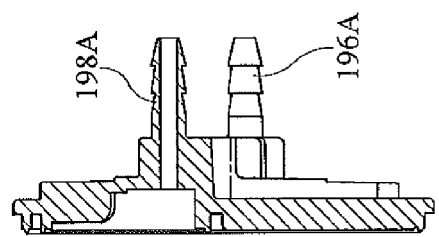
Figure 10I:
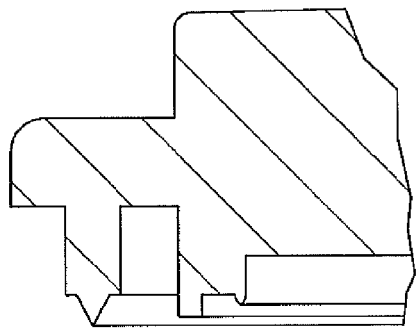
Figure 10F:
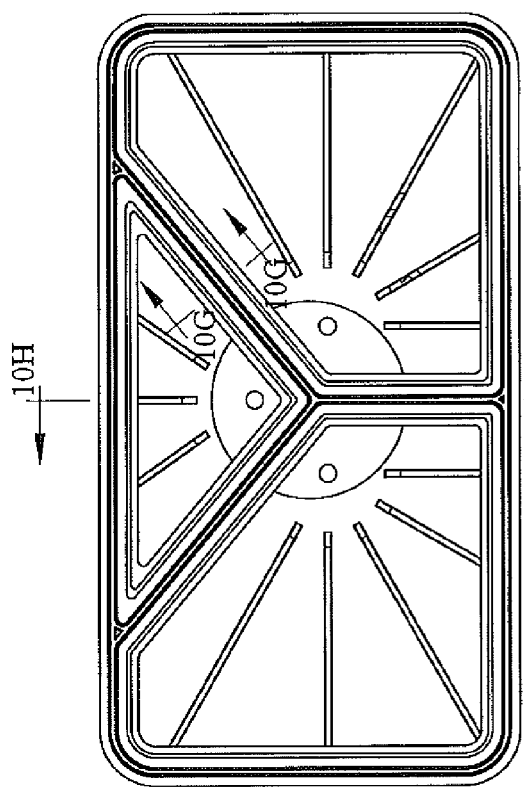
Figure 10G:
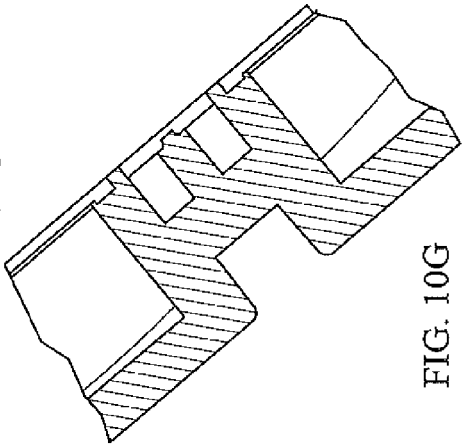
Figure 10M:
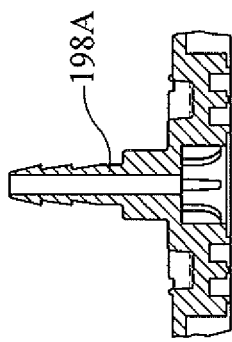
Figure 10J:
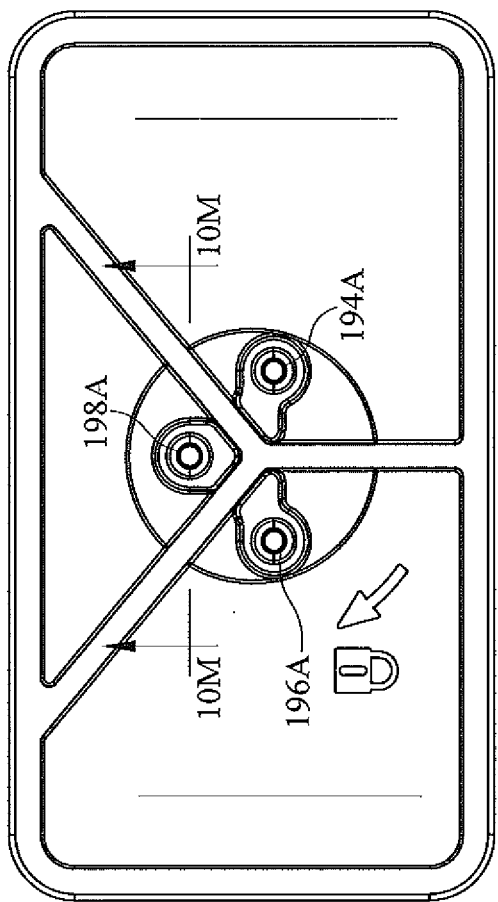
Figure 10L:
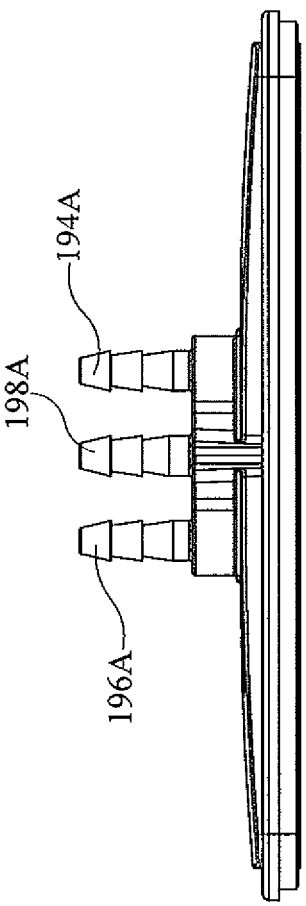
Figure 10K:
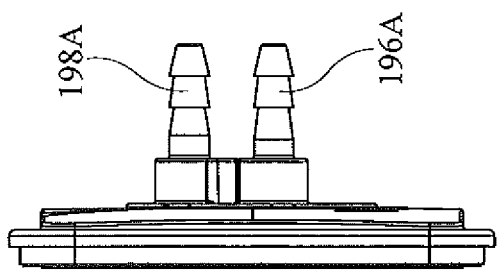
Figure 14:
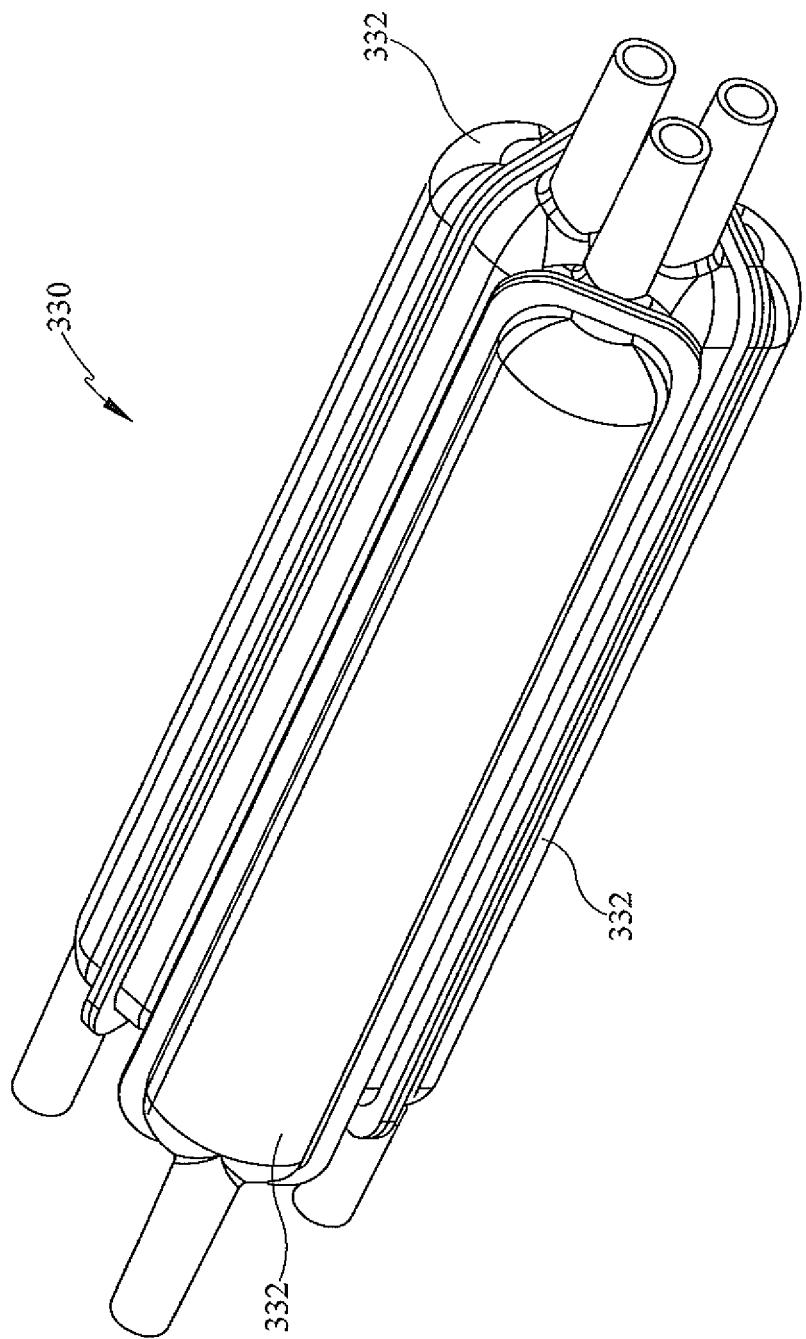
FIG. 14 is a perspective view of a filtration assembly comprised of three subassemblies.

FIG. 8 shows a circuit having a non-in-line filtration module 228. FIGS. 9A-10M show the module in detail. The module comprises a filter housing 230 comprising an inlet shell 232 which defines an input side of the housing, and an outlet shell 234 which defines an output side of the housing. The inlet and outlet shells include seal ribs 236. The inlet and outlet shells engage each other along the seal ribs and around their perimeters to define two or more mutually isolated filter compartments such as first, second and third compartments 244, 246, 248. The sides of each shell that face each other when so engaged are the interior sides (FIGS. 9A, 9E, 10A, 10E); the other side of each shell is an exterior side (FIGS. 9B, 9D, 10B, 10D) and faces outwardly when the shells are engaged with each other.

The inlet shell includes a gas inlet 184A, 186A, 188A in fluid communication with each of the filter compartments. The outlet shell includes a gas outlet 194A, 196A, 198A in fluid communication with each of the filter compartments. First, second and third filter elements 254, 256, 258 reside in each of the compartments intermediate the gas inlet to the compartment and the gas outlet from the compartment. The illustrated module has exactly three compartments with exactly one inlet and exactly one outlet in communication with each compartment. Inlets 184A, 186A, 188A, are analogous to inlets 184, 186, 188 already described in the context of connector unit 180 and are similarly arranged so that inlets 184A, 186A, 188A, tabs 200A and prong 202A define a filter module connector unit 180A on the filter housing. In particular, filter module connector unit 180A has a female side with first, second and third inlets 184A, 186A, 188A clustered together in a single unit 180A. Connector unit 180A also includes a pair of radially projecting tabs 200A and a key in the form of a prong 202A. When a user wishes to connect the circuit to control unit 12, of a host device (e.g. therapy device 10) the user ensures that connector disk 70 is in its "connect" orientation (FIG. 1D) and then pushes the female side of connector unit 180A (with transfer conduits 130, 132 and pressure sense line 150 preferably already connected to gas outlet projections 194A, 196A, 198A on outlet shell 234) onto outlet ports 74, 76, 78, of control unit 12. At the same time, prong 220A enters receptacle 74. The user then rotates filter module 228 counterclockwise, which causes connector disk 70 to also rotate and tabs 200A to slide through retainer openings 66 until the tabs encounter stops 64. The connector unit tabs are thus trapped behind retainer faces 60 so that the retainers resist unintended disconnection of connector unit 180A from the pneumatic control unit and so that outlet ports 74, 76, 78 are correctly aligned with tubes 84, 86, 88 (FIGS. 2-3). Because inlets 184A, 186A, 188A are all part of a single connector unit, the inlets are connectable in unison to the control unit so that each inlet registers with a prescribed port of the therapy device control unit. Prong 202A and receptacle 72 are in a common orientation so that the receptacle 72 will receive the prong and so that the connector unit inlets 184A, 186A, 188A will receive the outlet ports 74, 76, 78 only if the user is making a connection between a mutually compatible circuit and control unit. A circuit and a control unit that are incompatible with each other will have a prong and a receptacle oriented sufficiently differently that a proper connection cannot be made. Accordingly, the prong and receptacle constitute an error proofing feature. The principal difference between connector unit 180A and connector unit 180 is that connector unit 180A does not include serrated outlet projections 194A, 196A, 198A. Instead, the serrated outlets projecting from outlet shell 234 are analogous to serrated outlet projections 194, 196, 198 of connector unit 180.

When a host device, for example the respiratory therapy device 10 already described, uses the circuit and filter module of FIGS. 8-10M, filter housing 230 is intermediate the control unit outlet ports 74, 76, 78 and the transfer conduits 130, 132 and pressure sense line 150. The filter housing defines a first filter compartment 244 containing first filter element 254 and second filter compartment 246 containing second filter element 256. The housing has an input side represented by inlet shell 232 with a first inlet 184A in fluid communication with first control unit outlet port 74 and with first filter compartment 244. The inlet shell also has a second inlet 186A in communication with second control unit outlet port 76 and with second filter compartment 246. The inlet shell also has a third inlet 188A in fluid communication with third control unit port 78 and with third filter compartment 248. The housing also has an output side represented by output shell 234 with a first outlet 194A in fluid communication with first filter compartment 244 and first transfer conduit 130, a second outlet 196A in communication with second filter compartment 246 and with second transfer conduit 132, and a third outlet 198A in communication with third filter compartment 248 and with pressure sense line 150. The inlets 184A, 186A and outlets 194A, 196A establish fluid communication between the first and second control unit outlet ports 74, 76 and the first and second transfer conduits 130, 132 respectively. Inlet 188A and outlet 198A establish communication between third outlet port 78 and pressure sense line 150.

Each filter compartment has a plane geometric shape. For example compartment 248 is approximately triangular and compartments 244, 246 are five sided figures. The geometric shapes of all the compartments, taken collectively, are notionally arrangeable to approximately define a plane polygon, which in the example shown is a rectangle. It will be appreciated that "rectangle" includes the limit case of a square. In the example shown the shapes are not only notionally arrangeable as a plane polygon, but are actually arranged as a plane polygon. By constraining the shapes of the compartments to define a rectangle, the filtration elements 254, 256, 258 can be cut out of a larger sheet of filtration material with minimal waste. This advantage may also extend to other regular and nonregular plane polygons.

FIGS. 11A-11B show a filter module 270 whose housing is substantially circular and which is made up of an inlet shell 274 and an outlet shell 276 which, when assembled to each other, define exactly three similarly sized, sectors of a circle which serve as first, second and third filter compartments 284, 286, 288. Other compartment counts other than three can be employed. Inlet shell 274 includes a gas inlet 294, 296, 298 in fluid communication with each of the filter compartments. Outlet shell 276 includes a gas outlet 304, 306, 308 in fluid communication with each of the filter compartments. First, second and third filter elements (unnumbered) each of which is substantially congruent with the compartment, reside in each of the compartments intermediate the gas inlet to the compartment and the gas outlet from the compartment. Each compartment and filter element subtends an arc of about 120 degrees. The illustrated module has exactly three compartments with exactly one inlet and exactly one outlet in communication with each compartment. FIG. 12 shows a circular filter module similar to that of FIGS. 11A-11B but having two similarly sized compartments 286A, 288A and a third uniquely sized compartment 284A. FIG. 13 shows a circular filter module similar to that of FIGS. 11A-11B having two similarly sized compartments 320, 322.

Referring to FIGS. 14-17, a filtration assembly 330 comprises two or more filtration subassemblies 332. Each subassembly comprises an inlet shell 334 and an outlet shell 336 engaged with the inlet shell such that each subassembly has a longitudinal dimension L and a radial dimension R. The longitudinal dimension exceeds the radial dimension. As a result the subassemblies have an elongated form. The inlet shell is substantially identical to the outlet shell. A filter element 340 resides inside each subassembly and extends nonobliquely along the longitudinal dimension of the subassembly thereby dividing the interior of the subassembly into an inlet filter compartment 342 and an outlet filter compartment 344. Each subassembly also includes an inlet 360 in communication with the inlet compartment and an outlet 362 in communication with the outlet compartment. Inlet shell 334 and outlet shell 336 each have a substantially semicircular cross section so that when the shells are engaged with each other to form the subassembly, each subassembly has a substantially circular cross section.

FIG. 18 shows an alternative arrangement in which the filter element 340A extends obliquely along the longitudinal dimension of its subassembly to increase the available filtration area.

FIGS. 19-20 show another alternative arrangement in which one of the shells 334A has a cross section defined by a curved line segment 370 (such as a circular segment) and a straight line segment 372 connecting the ends of the curved segment. The other shell 336A has a cross section defined by three straight line segments 376, 378, 380, two of which subtend an angle $\alpha$ of about 120 degrees, but which may be other than 120 degrees. The subassemblies are arranged so that in the resultant filtration assembly shells 336A are radially inner shells and shells 334A are radially outer shells. The inner shells nest together to define a particularly compact filtration assembly whose curved segments 370 define or fit compactly within a circular or curved envelope of the filtration assembly.

Figure 21:
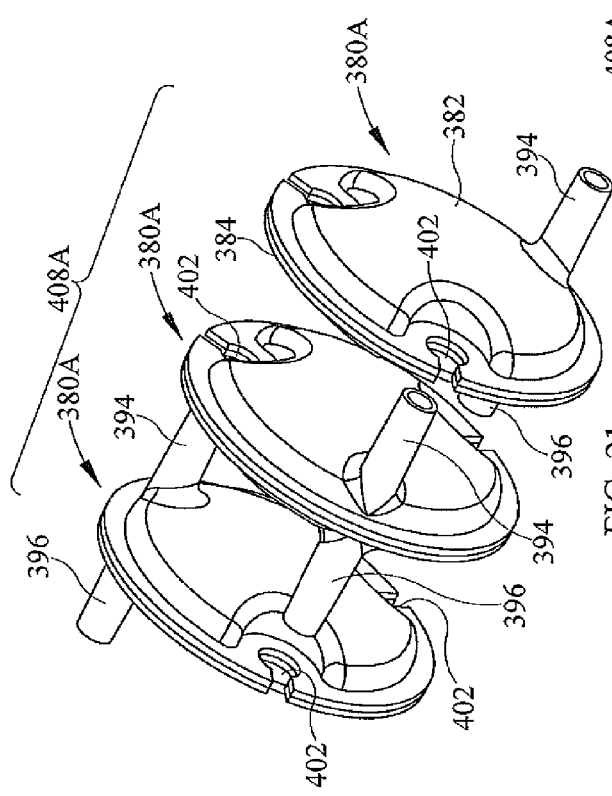
FIGS. 21-22 are an exploded perspective view and an exploded cross sectional side elevation view of a first variant of a filter assembly comprised of multiple filter units arranged in tandem, each filter unit being comprised of an inlet shell and an outlet shell.
Figure 22:
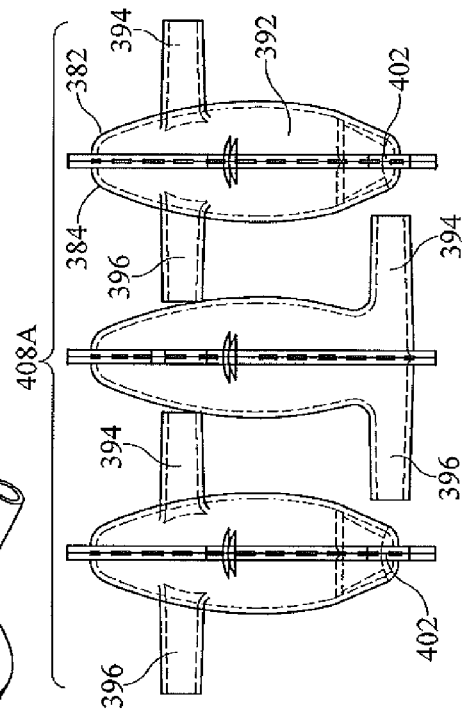
Figure 23:
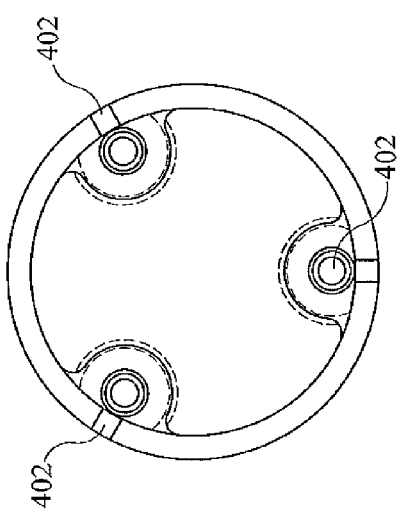
FIG. 23 is an end elevation view of the interior of one of the shells of FIGS. 20-21.

FIGS. 21-23 show one variant 380A of another filter unit. FIGS. 24-25 show another variant 380B. In both variants the filter unit comprises an inlet shell 382 engaged with an outlet shell 384 to comprise a housing 386 having a perimeter and an internal filter compartment 392. The inlet shell includes a single inlet 394 to the filter compartment. Inlet 394 projects outwardly from the inlet shell. Outlet shell 384 includes a single outlet 396 from the filter compartment. The outlet projects outwardly from the outlet shell. A filter element 400 resides in the compartment intermediate the inlet and the outlet. Inlet 394 and outlet 396 have an angular relationship with respect to each other. In the variant of FIGS. 21-23 the angular relationship is an angular offset of 0 degrees. In the variant of FIGS. 24-25 the angular offset is greater than 0 degrees. The housing has at least one bypass opening 402 penetrating therethrough. The opening or openings are angularly offset from the inlet and from the outlet and from each other.

Referring only to the first variant of FIGS. 21-23, the filter unit has N bypass slots where N≥2 whereby N+1 of such units can be arranged longitudinally in tandem with each other such that one or both of the inlet 394 and outlet 396 of each unit projects through a bypass slot of at least the next adjacent unit to define a filter assembly 408A. When so arranged, all but two of the N+1 units are interior units, one of the N+1 units is an upstream unit and one of the N+1 units is a downstream unit. The outlet of each interior unit projects through a bypass slot of all the units downstream of itself. The inlet to each interior unit projects through a bypass slot of all the units upstream of itself. The outlet of the upstream unit projects through a bypass slot of all the units downstream of itself. The inlet of the downstream unit projects through a bypass slot of all the units upstream of itself. In the specific example illustrated, N=2 and the bypass openings are angularly offset from each other by about 120 degrees and are angularly offset from the inlet by about 120 degrees.

Referring now only to the second variant of FIGS. 24-25, the filter unit comprises N bypass slots where N≥2 whereby N+1 of such units can be arranged longitudinally in tandem with each other such that one or both of the inlet and outlet of each filter unit projects through a bypass slot of at least the next adjacent unit to define a filter assembly. When so arranged all but two of the N+1 units are interior units, one of the N+1 units is an upstream unit and one of the N+1 units is a downstream unit. The outlet of each interior unit projects through a bypass opening of all the units downstream of itself. The inlet to each interior unit projects through a bypass opening of all the units upstream of itself. The outlet of the upstream unit projects through a bypass opening of all the units downstream of itself. The inlet of the downstream unit projects through a bypass opening of all the units upstream of itself. In the specific example illustrated N=2 and the inlet, the outlet and the bypass openings are equiangularly distributed.

In the embodiments of FIGS. 11-25 the inlet and outlet shells are identical to each other. As a result, manufacturing cost and complexity are simplified.

Although this disclosure refers to specific embodiments, it will be understood by those skilled in the art that various changes in form and detail may be made without departing from the subject matter set forth in the accompanying claims.

We claim:

1. A filtration module comprising:
 a filter housing defining two or more filter compartments, the housing having an input side with at least one gas inlet in fluid communication with each of the filter compartments and at least one gas outlet in fluid communication with each of the filter compartments;
 a filter element residing in each of the compartments intermediate the gas inlet to the compartment and the gas outlet from the compartment, wherein
 the inlets are clustered together in a single connector unit so that the inlets are connectable in unison to a host device and such that when connected to the host device each inlet registers with a prescribed port of the host device.

2. The module of claim 1 wherein the filter housing comprises an inlet shell which includes the inlets and an outlet shell which includes the outlets, the inlet and outlet shells engaged with each other to define the two or more compartments.

3. The module of claim 2 wherein the inlet shell and the outlet shell are substantially identical to each other.

4. The module of claim 2 in which the inlet shell and the outlet shell each have a perimeter and each include a seal rib, and wherein the inlet shell and the outlet shell engage each other along their seal ribs and also around their perimeters the engagement defining two or more mutually isolated filter compartments.

5. The module of claim 1 wherein the connector unit includes:
 1) a radially projecting tab engageable with the host device to resist unintended disconnection of the connector unit from the host device; and
 2) a key to resist inappropriate connection of the connector unit to the host device.

6. The module of claim 1 comprising exactly three compartments, exactly one inlet in communication with each compartment and exactly one outlet in communication with each compartment.

7. The module of claim 1 wherein the filter housing is substantially circular and the filter compartments are part-circular sectors.

8. The module of claim 1 in which each compartment has a plane geometric shape and the geometric shapes of all the compartments, taken collectively, are notionally arrangeable to approximately define a plane polygon.

9. The module of claim 8 in which the approximate plane polygon is a rectangle.

10. The module of claim 1 in which each compartment has a plane geometric shape and the geometric shapes of all the compartments, taken collectively, are arranged to approximately define a plane polygon.

11. The module of claim 10 in which the approximate plane polygon is a rectangle.

12. The module of claim 1 wherein the connector unit includes a radially projecting tab and a prong that projects past a plane of the inlets.

13. The module of claim 12 wherein the tab is configured to be trapped behind a retainer of a host device.

14. A filtration module comprising:
 a filter housing defining two or more filter compartments, the housing having an input side with at least one gas inlet in fluid communication with each of the filter compartments and at least one gas outlet in fluid communication with each of the filter compartments; and
 a filter element residing in each of the compartments intermediate the gas inlet to the compartment and the gas outlet from the compartment, wherein:
 the inlet are clustered together in a single connector unit which includes:
 1) a radially projecting tab engageable with the host device to resist unintended disconnection of the connector unit from the host device; and
 2) a key to resist inappropriate connection of the connector unit to the host device.

* * * * *